US005786374A

United States Patent [19]
Farooq et al.

[11] Patent Number: 5,786,374
[45] Date of Patent: Jul. 28, 1998

[54] BENZISOXAZOLE DERIVATIVES AND PESTICIDAL COMPOSITIONS CONTAINING THEM

[75] Inventors: Saleem Farooq, Arisdorf, Switzerland; Stephan Trah, Freiburg, Germany; René Zurflüh, Basel, Switzerland

[73] Assignee: Novartis Corporation, Summit, N.J.

[21] Appl. No.: 836,072

[22] PCT Filed: Oct. 23, 1995

[86] PCT No.: PCT/EP95/04154

§ 371 Date: May 1, 1997

§ 102(e) Date: May 1, 1997

[87] PCT Pub. No.: WO96/14305

PCT Pub. Date: May 17, 1996

[30] Foreign Application Priority Data

Nov. 3, 1994 [CH] Switzerland ................ 328/94

[51] Int. Cl.$^6$ .................. A61K 31/42; C07D 263/56
[52] U.S. Cl. ........................... 514/379; 548/241
[58] Field of Search ................ 548/241; 514/379

[56] References Cited

FOREIGN PATENT DOCUMENTS 0414153  2/1991  European Pat. Off. .
9218487  10/1992  WIPO .

Primary Examiner—Joseph McKane
Attorney, Agent, or Firm—Hesna J. Pfeiffer

[57] ABSTRACT

The present invention relates to benzisoxazole compounds, pesticidal compositions containing them, and their preparations thereof.

24 Claims, No Drawings

BENZISOXAZOLE DERIVATIVES AND PESTICIDAL COMPOSITIONS CONTAINING THEM

This application is a 371 of PCT/EP95/04154 filed Oct. 23, 1995.

The present invention relates to compounds of formula

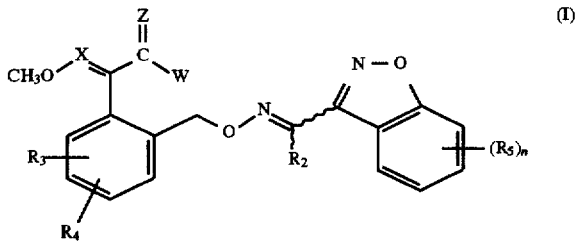

wherein a) X is CH, Z is oxygen and W is $OR_1$; or b) X is nitrogen, Z is oxygen and W is $OR_1$; or c) X is nitrogen, Z is oxygen, sulfur or sulfoxide (SO) and W is the $NHR_1$ group; and the other substituents have the following meanings:

$R_1$ is $C_1$–$C_4$alkyl; $C_3$–$C_4$alkenyl; $C_3$–$C_4$alkynyl;

$R_2$ is H, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or CN;

$R_3$ and $R_4$ are each independently of the other H, $C_1$–$C_4$alkyl, $C_1$–$C_4$alkoxy, OH, CN, $NO_2$, $Si(CH_3)_3$, $CF_3$ or halogen;

n is 0, 1, 2, 3 or 4;

$R_5$ is halogen, $C_1$–$C_4$alkyl, halo-$C_1$–$C_4$alkyl, unsubstituted or mono- to tetrasubstituted $C_1$–$C_4$alkylenedioxy, the substituents being selected from the group consisting of $C_1$–$C_4$alkyl and halogen; CN, $NO_2$, $XR_6$, phenyl or chlorophenyl;

X is O, O($C_1$–$C_4$alkylene), ($C_1$–$C_4$alkylene)O, $S(O)_m$, $S(O)_m$($C_1$–$C_4$alkylene), ($C_1$–$C_4$alkylene)$S(O)_m$ or $C_1$–$C_4$alkylene;

m is 0, 1 or 2;

$R_6$ is $C_1$–$C_6$alkyl; halo-$C_1$–$C_6$alkyl; $C_3$–$C_6$cycloalkyl; CN; $C_1$–$C_4$alkylene-Si($C_1$–$C_4$alkyl)$_3$; $C_2$–$C_6$alkenyl or $C_3$–$C_6$alkynyl which are each unsubstituted or substituted by 1 to 3 halogen atoms, or mono- to pentasubstituted aryl or heterocyclyl, the substituents being selected from the group consisting of halogen, $C_1$–$C_6$alkyl, halo-$C_1$–$C_6$alkyl, $C_1$–$C_6$alkoxy, halo-$C_1$–$C_6$alkoxy and CN; or

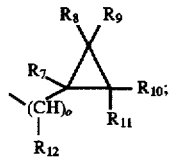

and wherein $R_7$, R8, $R_9$, $R_{10}$ and $R_{11}$ are each independently of one another H, halogen or $C_1$–$C_4$alkyl;

$R_{12}$ is H or $C_1$–$C_4$alkyl; and o is 0, 1, 2 or 3 and the possible E/Z isomers and mixtures of E/Z isomers thereof.

The invention further relates to a process for the preparation of, and to the use of, these compounds and E/Z isomers, to fungicidal and pesticidal compositions whose active ingredient is selected from said compounds and E/Z isomers, and to the preparation and use of said compositions.

Certain methoxyacrylic acid derivatives have been proposed in the literature for use as insecticidal and fungicidal compounds in pesticidal compositions. The biological properties of these known compounds, however, are not satisfactory in all respects in the field of pest control and fungicides, so that there is a need to provide further compounds having pesticidal properties, especially for controlling insects and representatives of the order Acarina, and fungicidal properties, especially for controlling phytopathogenic fungi. This object is achieved in the practice of this invention with the compounds of formula I.

Some compounds of formula I contain asymmetrically substituted carbon atoms, so that the compounds are obtained in optically active form. Owing to the presence of the olefinic and oximino double bonds, the compounds are obtained in the form of E and Z isomers. Furthermore, atropo-isomers of the compounds may also be obtained. Formula I will therefore be understood as encompassing all these possible isomeric forms as well as their mixtures, for example racemates and any mixtures of E/Z isomers.

Unless otherwise defined, the general terms employed throughout this specification have the meanings given hereinafter.

Unless otherwise defined, carbon-containing groups and compounds each contain from 1 to 6, preferably from 1 to 4, carbon atoms inclusive, and preferably contain 1 or 2 carbon atoms.

Alkyl as group per se as well as structural unit of other groups and compounds, as of haloalkyl, alkoxy and alkylthio, is either in straight-chain configuration, typically methyl, ethyl, propyl, butyl, pentyl, hexyl, heptyl or octyl, or in branched-chain configuration, typically isopropyl, isobutyl, sec-butyl, tert-butyl, isopentyl, neopentyl or isooctyl.

Alkenyl as group per se as well as structural unit of other groups and compounds, as of haloalkenyl, is either in straight-chain configuration, typically vinyl, 1-methylvinyl, allyl or 1-butenyl, or in branched-chain configuration, typically isopropenyl.

Alkynyl as group per se as well as structural unit of other groups and compounds, as of haloalkynyl, is either in straight-chain configuration, typically propargyl, 2-butynyl or 5-hexynyl, or in branched-chain configuration, typically 2-ethynylpropyl or 2-propargylisopropyl.

$C_3$–$C_6$Cycloalkyl is cyclopropyl, cyclobutyl, cyclopentyl or cyclohexyl.

Aryl is phenyl or naphthyl, preferably phenyl.

Heterocyclyl denotes a 5- to 7-membered aromatic or non-aromatic ring containing 1 to 3 hetero atoms selected from the group consisting of N, O and S. Aromatic 5- and 6-membered rings which contain a nitrogen atom as hetero atom and, in some cases, a further hetero atom, preferably nitrogen or sulfur, most preferably nitrogen.

Alkylenedioxy is —$OCH_2O$—, —$OCH_2CH_2O$—, —$OCH_2CH_2CH_2O$—, or —$OCH_2CH_2CH_2CH_2O$—.

Halogen as group per se as well as structural unit of other groups and compounds, as of haloalkyl, halocycloalkyl, haloalkenyl and haloalkynyl, is fluoro, chloro, bromo or iodo, preferably fluoro, chloro or bromo, more particularly fluoro or chloro, most preferably fluoro.

Halogen-substituted carbon-containing groups and compounds such as haloalkyl, halocycloalkyl, haloalkenyl or haloalkynyl, may be partially halogenated or perhalogenated. In the case of perhalogenation, the halogen substituents may be identical or different. Typical examples of haloalkyl as group per se as well as structural unit of other groups and compounds, as of halocycloalkyl and haloalkenyl, are methyl which is substituted by 1 to 3 fluorine, chlorine and/or bromine atoms, e.g. $CHF_2$ or $CF_3$; ethyl which is substituted by 1 to 5 fluorine, chlorine and/or bromine atoms, typically $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is substituted by 1 to 7 fluorine, chlorine and/or bromine atoms, typically $CH_2CHBrCH_2Br$, $CF_2CHFCF_3$, $CH_2CF_2CF_3$ or $CH(CF_3)_2$; and butyl or an isomer thereof which is substituted by 1 to 9 fluorine, chlorine and/or bromine atoms, typically $CF(CF_3)CHFCF_3$ or $CH_2(CF_2)_2CF_3$. Haloalkenyl is typically $CH_2CH=CHCl$, $CH_2CH=CCl_2$, $CH_2CF=CF_2$ or $CH_2CH=CHCH_2Br$. Haloalkynyl is typically $CH_2C\equiv CF$, $CH_2C\equiv CCH_2Cl$ or $CF_2CF_2C\equiv CCH_2F$.

Preferred embodiments within the scope of this invention are:

Compounds of formula Ia

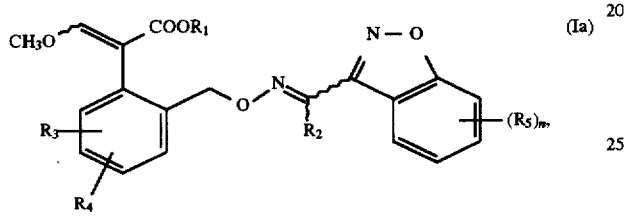

wherein $R_1$ is $C_1-C_4$alkyl;

$R_2$ is H, $C_1-C_4$alkyl, halo-$C_1-C_4$alkyl, cyclopropyl, $C_1-C_4$alkoxymethyl, $C_1-C_4$alkoxy, $C_1-C_4$alkylthio or CN;

$R_3$ and $R_4$ are each independently of the other H, $C_1-C_4$alkyl, $C_1-C_4$alkoxy, OH, CN, $NO_2$, $Si(CH_3)_3$, $CF_3$ or halogen;

n is 0, 1, 2, 3 or 4;

$R_5$ is halogen, $C_1-C_4$alkyl, halo-$C_1-C_4$alkyl, unsubstituted or mono- to tetrasubstituted $C_1-C_4$alkylenedioxy, the substituents being selected from the group consisting of $C_1-C_4$alkyl and halogen; CN; $NO_2$ or $XR_6$;

X is O, O($C_1-C_4$alkylene), ($C_1-C_4$alkylene)O, $S(O)_m$, $S(O)_m(C_1-C_4$alkylene), ($C_1-C_4$alkylene)$S(O)_m$ or $C_1-C_4$alkylene;

m is 0, 1 or 2;

$R_6$ is $C_1-C_6$alkyl, halo-$C_1-C_6$alkyl, $C_3-C_6$cycloalkyl, $C_2-C_6$alkenyl or $C_3-C_6$alkynyl which are each unsubstituted or substituted by 1 to 3 halogen atoms, unsubstituted or mono- to pentasubstituted aryl or heterocyclyl, the substituents being selected from the group consisting of halogen, $C_1-C_6$alkyl, halo-$C_1-C_6$alkyl, $C_1-C_6$alkoxy, halo-$C_1-C_6$alkoxy and CN; or

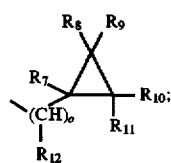

and wherein $R_7$, $R_8$, $R_9$, $R_{10}$ and $R_{11}$ are each independently of one another H, halogen or $C_1-C_4$alkyl;

$R_{12}$ is H or $C_1-C_4$alkyl; and o is 0, 1, 2 or 3. [Subgroup Ia].

Also:

Compounds of formula Ib

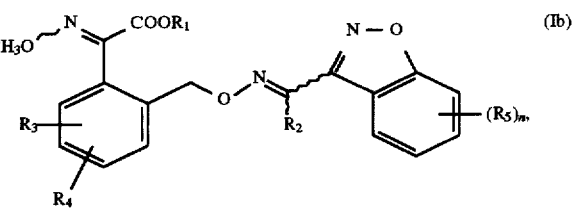

wherein $R_1$ is $C_1-C_4$alkyl;

$R_2$ is H, $C_1-C_4$alkyl, halo-$C_1-C_4$alkyl, cyclopropyl, $C_1-C_4$alkoxymethyl, $C_1-C_4$alkoxy, $C_1-C_4$alkylthio or CN;

$R_3$ and $R_4$ are each independently of the other H, $C_1-C_4$alkyl, $C_1-C_4$alkoxy, OH, CN, $NO_2$, $Si(CH_3)_3$, $CF_3$ or halogen;

n is 0, 1, 2, 3 or 4;

$R_5$ is halogen, $C_1-C_4$alkyl, halo-$C_1-C_4$alkyl, unsubstituted or mono- to tetrasubstituted $C_1-C_4$alkylenedioxy, the substituents being selected from the group consisting of $C_1-C_4$alkyl and halogen; CN; $NO_2$ or $XR_6$, phenyl or chlorophenyl;

X is O, O($C_1-C_4$alkylene), ($C_1-C_4$alkylene)O, $S(O)_m$, $S(O)_m(C_1-C_4$alkylene), ($C_1-C_4$alkylene)$S(O)_m$ or $C_1-C_4$alkylene;

m is 0, 1 or 2;

$R_6$ is $C_1-C_6$alkyl; halo-$C_1-C_6$alkyl; $C_3-C_6$cycloalkyl; CN; $C_1-C_4$alkylene-$Si(C_1-C_4$alkyl)$_3$; $C_2-C_6$alkenyl or $C_3-C_6$alkynyl which are each unsubstituted or substituted by 1 to 3 halogen atoms, or mono- to pentasubstituted aryl or heterocyclyl, the substituents being selected from the group consisting of halogen, $C_1-C_6$alkyl, halo-$C_1-C_6$alkyl, $C_1-C_6$alkoxy, halo-$C_1-C_6$alkoxy and CN; or

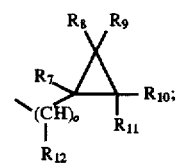

and wherein $R_7$, $R_8$, $R_9$, $R_{10}$ and $R_{11}$ are each independently of one another H, halogen or $C_1-C_4$alkyl;

$R_{12}$ is H or $C_1-C_4$alkyl; and o is 0, 1, 2 or 3. [Subgroup Ib]

Further:

compounds of formula Ic

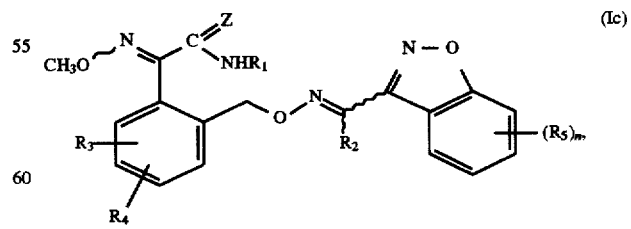

wherein $R_1$ is $C_1-C_4$alkyl; Z is oxygen, sulfur or sulfoxide;

$R_2$ is H, $C_1-C_4$alkyl, halo-$C_1-C_4$alkyl, cyclopropyl, $C_1-C_4$alkoxymethyl, $C_1-C_4$alkoxy, $C_1-C_4$alkylthio or CN;

$R_3$ and $R_4$ are each independently of the other H, $C_1-C_4$alkyl, $C_1-C_4$alkoxy, OH, CN, $NO_2$, $Si(CH_3)_3$, $CF_3$ or halogen;

n is 0, 1, 2, 3 or 4;

$R_5$ is halogen, $C_1-C_4$alkyl, halo-$C_1-C_4$alkyl, unsubstituted or mono- to tetrasubstituted $C_1-C_4$alkylenedioxy, the substituents being selected from the group consisting of $C_1-C_4$alkyl and halogen; CN; $NO_2$ or $XR_6$;

X is O, O($C_1-C_4$-alkylene), ($C_1-C_4$alkylene)O, S(O)$_m$, S(O)$_m$($C_1-C_4$alkylene), ($C_1-C_4$alkylene)S(O)$_m$ or $C_1-C_4$alkylene;

m is 0, 1 or 2;

$R_6$ is $C_1-C_6$alkyl; halo-$C_1-C_6$alkyl; $C_3-C_6$cycloalkyl; CN; $C_1-C_4$alkylene-Si($C_1-C_4$alkyl)$_3$; $C_2-C_6$alkenyl or $C_3-C_6$alkynyl which are each unsubstituted or substituted by 1 to 3 halogen atoms, or mono- to pentasubstituted aryl or heterocyclyl, the substituents being selected from the group consisting of halogen, $C_1-C_6$alkyl, halo-$C_1-C_6$alkyl, $C_1-C_6$alkoxy, halo-$C_1-C_6$alkoxy and CN; or

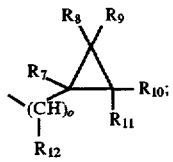

and wherein $R_7$, $R_8$, $R_9$, $R_{10}$ and $R_{11}$ are each independently of one another H, halogen or $C_1-C_4$alkyl;

$R_{12}$ is H or $C_1-C_4$alkyl; and o is 0, 1, 2 or 3. [Subgroup Ic].

Further preferred embodiments are:

(1) a compound of formula I or Ia, wherein
$R_1$ is $C_1-C_2$lkyl,
preferably methyl;

(2) a compound of formula I or Ia, wherein
$R_2$ is H, $C_1-C_4$alkyl, halo-$C_1-C_4$alkyl, cyclopropyl, $C_1-C_4$alkylthio or CN,
preferably $C_1-C_2$alkyl, halo-$C_1-C_2$alkyl, cyclopropyl, $C_1-C_2$alkylthio or CN,
most preferably $C_1-C_2$alkyl, halomethyl, cyclopropyl, methylthio or CN;

(3) a compound of formula I or Ia, wherein
$R_3$ is H, $C_1-C_2$alkyl, $C_1-C_2$alkoxy, CN, $NO_2$, $CF_3$ or halogen,
preferably H, $C_1-C_2$alkyl, $C_1-C_2$alkoxy, $CF_3$ or halogen,
most preferably H, methyl, methoxy, chloro or fluoro;

(4) a compound of formula I or Ia, wherein
$R_4$ is H, $C_1-C_2$alkyl, $C_1-C_2$alkoxy, CN, $NO_2$, $CF_3$ or halogen,
preferably H, $C_1-C_2$alkyl, $C_1-C_2$alkoxy, $CF_3$ or halogen,
most preferably H, methyl, methoxy, chloro or fluoro;

(5) a compound of formula I or Ia, wherein
n is 0, 1, 2 or 3,
preferably 0, 1 or 2,
most preferably 0 or 1;

(6) a compound of formula I or Ia, wherein
$R_5$ is halogen, $C_1-C_4$alkyl, halo-$C_1-C_4$alkyl, CN, $NO_2$ or $XR_6$,
preferably halogen, $C_1-C_4$alkyl, halo-$C_1-C_4$alkyl or $XR_6$, most preferably fluoro, chloro, $C_1-C_2$alkyl, halo-$C_1-C_2$alkyl or $XR_6$;

(7) a compound of formula I or Ia, wherein
X is O, O($C_1-C_2$alkylene), ($C_1-C_2$alkylene)O, S(O)$_m$, S(O)$_m$($C_1-C_2$alkylene),
($C_1-C_2$alkylene)S(O)$_m$ or $C_1-C_2$alkylene,
preferably O, O($C_1-C_2$alkylene), ($C_1-C_2$alkylene)O or $C_1-C_2$alkylene,
most preferably O or O(methylene);

(8) a compound of formula I or Ia, wherein
m is 0 or 1,
preferably 0;

(9) a compound of formula I or Ia, wherein
$R_6$ is $C_1-C_4$alkyl, halo-$C_1-C_4$alkyl, cyclopropyl, $C_2-C_4$alkenyl or $C_3-C_4$alkynyl which are each unsubstituted or substituted by 1 to 3 halogen atoms, or mono- to pentasubstituted aryl or heterocyclyl, the substituents being selected from the group consisting of halogen, $C_1-C_4$alkyl, halo-$C_1-C_4$alkyl, $C_1-C_4$alkoxy, halo-$C_1-C_4$alkoxy and CN; or

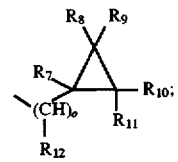

preferably $C_1-C_2$alkyl, halo-$C_1-C_2$alkyl, cyclopropyl, $C_2-C_4$alkenyl or $C_3-C_4$alkynyl which are each unsubstituted or substituted by 1 to 3 halogen atoms, or mono- to pentasubstituted aryl or heterocyclyl, the substituents being selected from the group consisting of halogen, $C_1-C_2$alkyl, halo-$C_1-C_2$alkyl, $C_1-C_2$alkoxy, halo-$C_1-C_2$alkoxy and CN; or

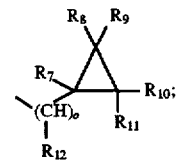

most preferably methyl, halomethyl, $C_2-C_3$alkenyl or propynyl which are each unsubstituted or substituted by 1 or 2 halogen atoms, or unsubstituted or monosubstituted phenyl, the substituents being selected from the group consisting of halogen, methyl, halomethyl, methoxy and CN;

(10) a compound of formula I or Ia, wherein
$R_7$ is H or $C_1-C_2$alkyl,
preferably H or methyl,
most preferably H;

(11) a compound of formula I or Ia, wherein
$R_8$ is H or halogen,
preferably bromo, chloro or fluoro,
most preferably chloro or fluoro;

(12) a compound of formula I or Ia, wherein
$R_9$ is H or halogen,
preferably bromo, chloro or fluoro,
most preferably chloro or fluoro;

(13) a compound of formula I or Ia, wherein
$R_{10}$ is H or $C_1-C_2$alkyl,
preferably H;

(14) a compound of formula I or Ia, wherein $R_{11}$ is H or $C_1$–$C_2$alkyl,
preferably H;

(15) a compound of formula I or Ia, wherein
$R_{12}$ is H or $C_1$–$C_2$alkyl,
preferably H;

(16) a compound of formula I or Ia, wherein
o is 0 or 1,
preferably 1;

(17) a compound of formula I or Ia, wherein
$R_1$ is $C_1$–$C_2$alkyl,
$R_2$ is $C_1$–$C_2$alkyl, halo-$C_1$–$C_2$alkyl, cyclopropyl, $C_1$–$C_2$alkylthio or CN,
$R_3$ and $R_4$ are each independently of the other H, $C_1$–$C_2$alkyl, $C_1$–$C_2$alkoxy, $CF_3$ or halogen,
n is 0, 1 or 2,
$R_5$ is halogen, $C_1$–$C_4$alkyl, halo-$C_1$–$C_4$alkyl or $XR_6$,
X is O, O($C_1$–$C_2$alkylene), ($C_1$–$C_2$alkylene)O,
$R_6$ is $C_1$–$C_2$alkyl, halo-$C_1$–$C_2$alkyl, cyclopropyl, $C_2$–$C_4$alkenyl or $C_3$–$C_4$alkynyl which are each unsubstituted or substituted by 1 to 3 halogen atoms, unsubstituted or mono- or disubstituted phenyl, the substituents being selected from the group consisting of halogen, $C_1$–$C_2$alkyl, halo-$C_1$–$C_2$alkyl, $C_1$–$C_2$alkoxy, halo-$C_1$–$C_2$alkoxy and CN; or

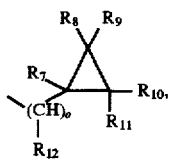

$R_7$ is H or methyl,
$R_8$ and $R_9$ are each independently of the other bromo, chloro or fluoro,
$R_{10}$, $R_{11}$ and $R_{12}$ are each independently of one another H or $C_1$–$C_2$alkyl, and
o is 0 or 1;

(18) a compound of formula I or Ia, wherein
$R_1$ is methyl,
$R_2$ is $C_1$–$C_2$alkyl, halomethyl, cyclopropyl, methylthio or CN,
$R_3$ and $R_4$ are each independently of the other H, methyl, methoxy, chloro or fluoro,
n is 0 or 1,
$R_5$ is fluoro, chloro, $C_1$–$C_2$alkyl, halo-$C_1$–$C_2$alkyl or $XR_6$,
X is O or O(methylene), and
$R_6$ is methyl, halomethyl, $C_2$–$C_3$alkenyl or propynyl which are each unsubstituted or substituted by 1 or 2 halogen atoms, or unsubstituted or monosubstituted phenyl, the substituents being selected from the group consisting of halogen, methyl, halomethyl, methoxy and CN;

Particularly preferred within the scope of this invention are the compounds of formula I listed in Tables 3, 4, 5, 6 and 7, and the E/Z isomers thereof whenever obtained.

Preferred specific compounds within the scope of the invention are methyl 2-[[[(1-{1,2-benzisoxazol-3-yl}ethylidene)amino]oxy]methyl]-α-(methoxymethylene) phenylacetate (compound 3.1), methyl 2-[[[(1-{6-methoxy-1,2-benzisoxazol-3-yl}ethylidene)amino]oxy]methyl]-α-(methoxymethylene)phenylacetate (compound 3.2), methyl 2-[[[(1-{6-[(2,2-dichlorocyclopropyl)methoxy]- 1,2-benzisoxazol-3-yl}ethylidene)amino]oxy]methyl]-α-(methoxymethylene)phenylacetate (compound 3.3), methyl α-(methoxymethylene)-2-[[[(1-{6-[3-(trifluoromethyl)benzyloxy]-1,2-benzisoxazol-3-yl}ethylidene)amino]oxy] methyl]phenylacetate (compound 3.4), methyl α-(methoxymethylene)-2-[[[(1 -{6-[2-propenyloxy]-1,2-benzisoxazol-3-yl}ethylidene)amino]oxy]methyl] phenylacetate (compound 3.5), methyl α-(methoxymethylene)-2-[[[(1-{6-[2-propynyloxy]-1,2-benzisoxazol-3-yl }ethylidene)amino]oxy]methyl] phenylacetate (compound 3.6), methyl α-(methoxymethylene)-2-[[[(1-{6-[4-(trifluoromethyl)benzyloxy]-1,2-benzisoxazol-3-yl}ethylidene)amino]oxy] methyl]phenylacetate (compound 3.7), methyl α-(methoxymethylene)-2-[[[(1-{6-[2-(trifluoromethyl)benzyloxy]-1,2-benzisoxazol-3-yl}ethylidene)amino]oxy] methyl]phenylacetate (compound 3.8), methyl 2-[[[(1-{5-methoxy-1,2-benzisoxazol-3-yl}ethylidene)amino]oxy] methyl]-α-(methoxymethylene)phenylacetate (compound 3.9), 2-[[[(1 -{6-[3,3-dichloro-2-propenyloxy]-1,2-benzisoxazol-3-yl}ethylidene)amino]oxy]methyl]-α-(methoxymethylene)phenylacetate (compound 3.10), and the two E/Z isomers of methyl 2-[[[(1-{6-[1,1,2,3,3,3-hexafluoropropoxy]-1,2-benzisoxazol-3-yl}ethylidene) amino]oxy]methyl]-α-(methoxymethylene)phenylacetate (compounds 3.11A and 3.11B).

Among the particularly preferred compounds are the compound of Example P6, methyl 2-[[[(1-{1,2-benzisoxazol-3-yl}ethylidene)amino]oxy]methyl]-α-(methoxymethylene)phenylacetate (compound 3.1) and the E/Z isomers thereof as well as the 5-chloro-1,2-benzisoxazol-3-yl derivative thereof (compound 3.17).

The invention further relates to the process for the preparation of the compounds of formula I and the E/Z isomers thereof, which comprises reacting a compound of formula

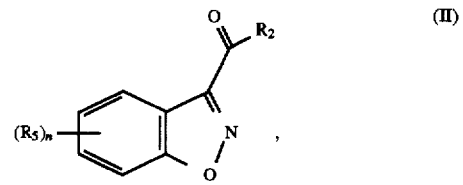

which is either known or can be prepared in analogy to corresponding known compounds, and wherein $R_2$ and $R_5$ are as defined for formula I, preferably in the presence of a base, with hydroxylamine hydrochloride, and reacting the intermediate, which may or may not be isolated, in the presence of a base, with a compound of formula

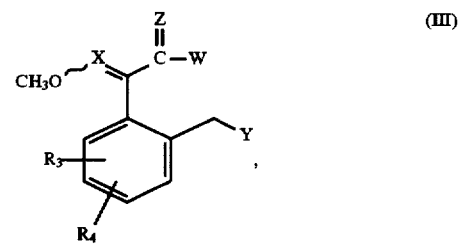

which is either known or can be prepared in analogy to corresponding known compounds, and wherein X, Z, W, $R_3$ and $R_4$ are as defined in connection with formula I, and Y is halogen, preferably chloro or bromo, and, if desired, converting a compound of formula I obtainable by the process of the invention or in another manner or an E/Z isomer thereof into another compound of formula I or an E/Z isomer thereof, separating a mixture of E/Z isomers obtainable by the process of the invention and isolating the desired isomer.

With respect to the starting materials referred to above, what has been stated with reference to E/Z isomers of compounds I applies by analogy to the E/Z isomers of said starting materials.

The reactions described above and subsequently are carried out in per se known manner, conveniently in the absence or, usually, in the presence of a suitable solvent or diluent or of a mixture thereof and, as required, with cooling at room temperature or with heating, e.g. in the temperature range from c. 0° C. to the boiling temperature of the reaction medium, preferably in the range from c. 20° C. to c. +120° C., most preferably from 60° C. to 80° and, if necessary, in a closed reactor under pressure in an inert gas atmosphere and/or under anhydrous conditions. Particularly advantageous reaction conditions will be found in the Examples.

The starting materials required for the synthesis of compounds I and, where appropriate, of their E/Z isomers, and referred to above and subsequently, are known or can be prepared by per se known methods, conveniently in accordance with the particulars given below.

Suitable bases for facilitating the reaction are typically alkylamines, alkylenediamines, unsubstituted or N-alkylated, unsaturated or saturated cycloalkylamines as well as basic heterocycles. Typical examples of such bases are triethylamine, diisopropylethylamine, triethylenediamine, N-cyclohexyl-N,N-dimethylamine, N,N-diethylaniline, pyridine, 4-(N,N-dimethylamino) pyridine, quinuclidine, N-methylmorpholine such as 1,5-diaza-bicyclo[5.4.0]undec-5-ene (DBU).

The reactants can be reacted with one another per se, i.e. without addition of a solvent or diluent, conveniently in the melt. Usually, however, the addition of an inert solvent or diluent or of a mixture thereof, is useful. Illustrative examples of such solvents or diluents are: aromatic, aliphatic and alicyclic hydrocarbons, and halogenated hydrocarbons such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters such as ethyl acetate; ethers such as diethyl ether, dipropyl ether, diisopropyl ether, dibutyl ether, tert-butylmethyl ether, ethylene glycol monomethyl ether, ethylene glycol monoethyl ether, ethylene glycol dimethyl ether, dimethoxy diethyl ether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric triamide; nitriles such as acetonitrile or propionitrile; and sulfoxides such as dimethyl sulfoxide. If the reaction is carried out in the presence of a base, it is also possible to use as solvent or diluent a base that is used in excess, for example triethylamine, pyridine, N-methylmorpholine or N,N-diethylaniline.

The reaction is conveniently carried out in the temperature range from c. 0° C. to c. +120° C., preferably from c.20° C. to c. +80° C.

In a preferred embodiment of the process, a compound of formula II is reacted in the temperature range from 20° to 120° C., preferably at 110° C., in a basic solvent, preferably pyridine, with hydroxylamine or hydroxylamine hydrochloride, preferably hydroxylamine hydrochloride, the product is isolated and reacted with a compound of formula III in the temperature range from 20° to 100° C., preferably from 60° to 80° C., in an inert solvent, e.g. acetonitrile, in the presence of a base, preferably an inorganic base, more particularly potassium carbonate.

Compounds of formula II are obtained in accordance with the method described in J. Heterocyclic Chem. 18 (1981), p. 347.

They can also be obtained by oximating an acetophenone derivative having an ortho-positioned hydroxyl group in the phenyl ring

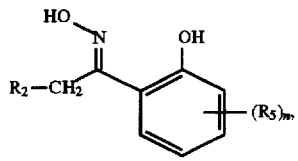

acylating the oxime and effecting basic cyclisation to give the intermediates of formula

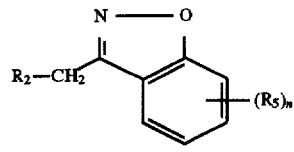

with subsequent chlorination or bromination of the methylene group, replacement of the halogen atom by an —OAc (acyloxy) group, saponification to the $R_2$-CH(OH) side-chain and oxidation of the hydroxyl group to give the ketone.

Furthermore, the already oximated secondary products of the compounds of formula II can be obtained direct by a short route by stepwise oximation of an acetophenone derivative which is halogenated, preferably fluorinated or chlorinated, in ortho-position in the phenyl ring

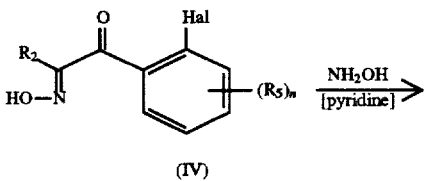

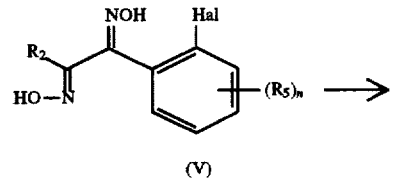

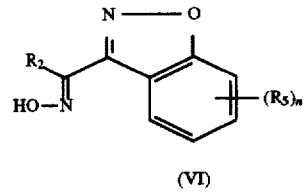

For the first oximation of the $R_2$—$CH_2$— side-chain it is convenient to use a nitrite, e.g. an alkyl nitrite, typicaly isopentyl nitrite/HCl, in an inert solvent such as a hydrocarbon or an ether, e.g. dioxane or tetrahydrofuran. The temperature range is from 10° C. to 80° C., preferably room temperature.

For the second oximation, namely that of the keto group in the intermediate IV, hydroxylamine or a hydroxylamine salt, e.g. $NH_2OH\cdot HCl$, is used in the presence of a base such as pyridine which may also be used as solvent. Further solvents or diluents may also be used, conveniently an ether or alcohol such as ethanol. The temperature is in the range from c. 20° to 180° C., preferably the reflux temperature of the reaction mixture.

The last step of the cyclisation to the benzisoxazole oxime VI is carried out with a strong base such as a hydroxide or carbonate of an alkali metal or alkaline earth metal in alcoholic or aqueous/alcoholic solution, conveniently in ethanol (q.v. Preparatory Examples P7 and P9). The intermediate VI can be reacted with intermediates III to give the final products of formula I.

It is also possible to react the intermediates III with the intermediates of formula IV by another process variant and then to carry out the cyclisation to the benzisoxazole in accordance with IV→V→VI. In this variant, the halogen atom in the intermediate IV can also be replaced by an acetone-oxime radical and the cyclisation carried out therewith. (q.v. Example P8).

The compounds I, II and III can be obtained in the form of one of the possible isomers or as a mixture thereof, e.g. depending on the number and absolute and relative configuration of the asymmetrical carbon atoms, as pure isomers, e.g. antipodes and/or diastereoisomers, or as mixtures of isomers, e.g. mixtures of enantiomers, e.g. racemates, mixtures of diastereoisomers or mixtures of racemates. The invention thus relates to the pure isomers as well as to all possible mixtures of isomers.

Mixtures of enantiomers such as racemates can be resolved into their optical antipodes by known methods, typically by recrystallisation from an optically active solvent, by chromatography on chiral adsorbants, e.g. high-pressure liquid chromatography (HPLC) on acetyl cellulose, with the aid of suitable microorganisms, by cleavage with specific immobilised enzymes, via the formation of inclusion compounds, e.g. using chiral crown ethers, in which case only one enantiomer is complexed.

The compounds I, II and III can also be obtained in the form of their hydrates and/or include other compounds, for example solvents used for the crystallisation of compounds obtained in solid form.

The invention relates in particular to the preparatory process described in Example P6.

The invention likewise relates to starting materials and intermediates which are novel and used in the practice of this invention for the preparation of the compounds of formula I, in particular the compounds of formula II and III, to their use and to processes for their preparation. In particular, the compounds of formula II can be prepared in analogy to Examples P1 to P4 and P9.

It has been found that the compounds of formula I have, for practical purposes, a particularly advantageous microbicidal spectrum for controlling phytopathogenic microorganisms, especially fungi. They have very useful curative, preventive and, in particular, systemic properties, and are used for protecting numerous cultivated plants. The compounds of formula I can be used to inhibit or destroy the pests which occur on plants or parts of plants (fruit, blossoms, leaves, stems, tubers, roots) in different crops of useful plants, while at the same time the parts of plants which grow later are also protected from attack by phytopathogenic microorganisms.

The compounds of formula I can also be used as dressing agents for protecting seeds (fruit, tubers, grains) and plant cuttings against fungal infections as well as against phytopathogenic fungi which occur in the soil.

The compounds of formula I are effective against the phytopathogenic fungi belonging to the following classes: Fungi imperfecti (in particular Botrytis and also Pyricularia, Helminthosporium, Fusarium, Septoria, Cercospora, Cercosporella and Altemaria); Basidiomycetes (e.g. Rhizocotonia, Hemileia, Puccinia). They are also effective against the class of the Ascomycetes (e.g. Venturia and Erysiphe, Podosphaera, Monilinia and Uncinula), and especially against that of the Oomycetes (e.g. Phytophthora, Peronospora, Bremia, Pythium, Plasmopara).

The novel compounds of formula I are well tolerated by warm-blooded animals, fish and plants and are moreover useful active ingredients for use in the field of pest control. In particular, the novel compounds are effective against the insects that occur in crop plants and ornamentals in agriculture and horticulture, in particular in crops of cotton, vegetables and fruit, and in forestry. The novel compounds are particularly suitable for controlling insects in fruit and vegetable crops, especially for controlling plant-injurious insects such as *Spodoptera littoralis*, *Heliothis virescens*, *Diabrotica balteata* and *Crocidolomia binotalis*. Further fields of use of the compounds of this invention are in the storage and material protection sectors as well as the hygiene sector, especially the protection of domestic animals and productive livestock. The novel compounds are effective against all or individual development stages of normal sensitive as well as resistant species of pests. The activity of the compounds of formula I may be observed in an immediate kill of the pests or sometime later, for example in moulting or in diminished oviposition and/or hatching rate.

The above-mentioned pests typically include those of the order Lepidoptera,
of the order Coleoptera,
of the order Orthoptera,
of the order Isoptera,
of the order Psocoptera,
of the order Anoplura,
of the order Mallophaga,
of the order Thysanoptera,
of the order Heteroptera,
of the order Homoptera,
of the order Hymenoptera,
of the order Diptera, for example *Aedes spp., Antherigona soccata, Bibio hortulanus, Calliphora erythrocephala, Ceratitis spp., Chrysomyia spp., Culex spp., Cuterebra spp., Dacus spp., Drosophila melanogaster* and others,
of the order Siphonaptera, and
of the order Thysanura.

The good pesticidal action of the novel compounds corresponds to a mortality of at last 50–60% of these pests.

The activity of the compounds of this invention and of the compositions containing them can be substantially broadened and adapted to prevailing circumsances by addition of other insecticides. Examples of suitable additives typically include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations in polymeric substances. As with the type of the compositions, the methods of application, such as spraying, atomising, dusting, scattering, coating or pouring, are chosen in accordance with the intended objectives and the prevailing circumstances.

The formulations, i.e. the compositions, preparations or mixtures containing the compound of formula I and, where appropriate, a solid or liquid adjuvant, are prepared in known manner, conveniently by homogeneously mixing and/or grinding the active ingredient with extenders, as with solvents or solid carriers, or surface-active compounds (surfactants).

Suitable solvents are: aromatic hydrocarbons, the fractions containing 8 to 12 carbon atoms, typically xylene mixtures or substituted naphthalenes, phthalates such as dibutyl or dioctyl phthalate, aliphatic hydrocarbons such as cyclohexane or paraffins; also alcohols and glycols and their ethers and esters, such as ethanol, diethylene glycol, 2-methoxyethanol or 2-ethoxyethanol, ketones such as cyclohexanone, isophorone or diacetone alcohol, strongly polar solvents such as N-methyl-2-pyrrolidone, dimethyl sulfoxide or N,N-dimethylformamide, as well as vegetable oils or epoxidised vegetable oils such as epoxidised rapeseed oil, castor oil, coconut oil or soybean oil; or in some cases also silicone oils.

The solid carriers typically used for dusts and dispersible powders are usually natural mineral fillers such as calcite, talcum, kaolin, montmorillonite or attapulgite. To improve the physical properties it is also possible to add highly dispersed silica or highly dispersed absorbent polymers. Suitable granulated adsorptive carriers are porous types such as pumice, broken brick, sepiolite or bentonite; and suitable nonsorbent carriers are materials such as calcite or sand. In addition, a great number or pregranulated materials of inorganic or organic nature can be used, e.g. especially dolomite or pulverised plant residues.

Depending on the nature of the compound of formula I, or combination of formula I with other insecticides, to be formulated, suitable surface-active compounds are nonionic, cationic and/or anionic surfactants having good emulsifying, dispersing and wetting properties. The term "surfactants" will also be understood as comprising mixtures of surfactants.

The pesticidal compositions usually contain 0.1 to 99% by weight, preferably 0.1 to 95% by weight, of a compound of formula I or a combination of said compound with other insecticides, and 1 to 99.9% by weight, preferably 5 to 99.9 by weight, of a solid or liquid adjuvant, and 0 to 25% by weight, preferably 0.1 to 25% by weight, of a surfactant (the percentages are in each case by weight). Whereas commercial products will preferably be formulated as concentrates, the end user will normally use dilute formulations. Typical rates of application will be in the range from 0.1 to 1000 ppm, preferably from 0.1 to 500 ppm of active ingredient. The rates of application per hectare are usually from 1 to 1000 g a.i./ha, preferably from 25 to 500 g a.i./ha.

The compositions may also contain further ingredients such as stabilisers, typically vegetable oils or epoxidised vegetable oils (e.g. epoxidised coconut oil, rapeseed oil or soybean oil), antifoams, e.g. silicone oil, preservatives, viscosity regulators, binders and/or tackifiers, as well as fertilisers or other chemical agents to obtain special effects.

The invention is illustrated in more detail by the following non-limitative Examples.

PREPARATORY EXAMPLES

Example P1
1-(1,2-Benzisoxazol-3-yl)ethanone (compound 1.1 in Table 1)

a) 15 g of 1-(2-hydroxyphenyl)-1-propanone are added dropwise to 170 ml of a 40% aqueous solution of potassium hydroxide. To this emulsion are then added, in increments, 31.2 g of hydroxylamine hydrochloride and the mixture is stirred for 4 h at 0°–5° C. The reaction mixture is then acidified with 150 ml of concentrated hydrochloric acid, the precipitated product is isolated by filtration, washed with water and dried, giving 1-(2-hydroxyphenyl)-1-propanone oxime having a melting point of 88°–90° C.

b) A mixture of 11 g of 1-(2-hydroxyphenyl)-1-propanone oxime and 22 ml of acetic anhydride is heated briefly to 45° C. and then poured on to a mixture of ice/water. The precipitated product is isolated by filtration, washed with water and dried under vacuum, giving 1-(2-hydroxphenyl) -1-propanone-O-acetyloxime having a melting point of 86°–90° C.

c) A mixture of 12.2 g of 1-(2-hydroxyphenyl)-1-propanone-O-acetyloxime and 120 ml of pyridine is refluxed for 3 h. After cooling, the reaction mixture is poured on to a mixture of ice/water and acidified with c. 130 ml of concentrated hydrochloric acid. After extraction with ethyl acetate, the organic phase is washed three times with water and once with a saturated solution of sodium chloride, dried over sodium sulfate and concentrated under vacuum. The crude product is purified by chromatography over silica gel with ethyl acetate/hexane (1:3) to give 3-ethyl-1,2-benzisoxazole having a refractive index $n_D^{20}$ of 1.5403.

d) A mixture of 5.3 g of 3-ethyl-1,2-benzisoxazole, 6.4 g of N-bromosuccinimide and 50 ml of carbon tetrachloride is refluxed for 1 h. Afterwards c. 50 mg of α,α-azoisobutyronitrile are added and the mixture is refluxed for a further 1 h. After cooling and filtering the mixture, the filtrate is concentrated under vacuum. The crude product is purified by chromatography over silica gel with ethyl acetate/hexane (1:1) to give 3-(1-bromoethyl)-1,2-benzisoxazole as an oil.

e) A mixture of 5.6 g of 3-(1-bromoethyl)-1,2-benzisoxazole, 2.4 g of potassium acetate, 2.1 g of N,N,N, N-tetramethylethylenediamine and 50 ml of acetonitrile are refluxed for 14 h. After cooling and filtering the mixture, the filtrate is concentrated under vacuum and diluted with diethyl ether. The ether phase is washed once with water, then twice with a 10% solution of hydrochloric acid and finally washed once with a saturated solution of sodium chloride, dried over sodium sulfate and concentrated. The crude product is purified by chromatography over silica gel with ethyl acetate/hexane (1:3) to give 3-(1-acetoxyethyl)-1,2-benzisoxazole having a refractive index $n_D^{20}$ of 1.5229.

f) A mixture of 2.6 g of 3-(1-acetoxyethyl)-1,2-benzisoxazole, 0.9 g of potassium hydroxide, 40 ml of ethanol and 3 ml of water is stirred for 1 h at room temperature. The reaction mixture is then concentrated under vacuum and diluted with water. This aqueous phase is extracted three times with diethyl ether, the combined ethereal extracts are then washed with a saturated solution of sodium chloride and dried over sodium sulfate, giving 1-(1,2-benzisoxazol-3-yl)ethanol as an oil having a refractive index $n_D^{20}$ of 1.5555.

g) A mixture of 1.1 g of sodium bichromate dihydrate and 0.8 ml of sulfuric acid in 5 ml of water is slowly added dropwise to 1.6 g of 1-(1,2-benzisoxazol-3-yl)ethanol in 5 ml of diethyl ether. This mixture is stirred for 1 hour at room temperatur and then, with ice cooling, 50 ml of water are added and extraction wth diethyl ether is carried out three times. The combined ethereal extracts are washed once with a saturated solution of sodium bicarbonate, once with water and finally once with a saturated solution of sodium chloride, dried over sodium sulfate and concentrated under vacuum. The crude product is purified by chromatography over silica gel with ethyl acetate/hexane (1:3), giving 1-(1, 2-benzisoxazol-3-yl)ethanone having a melting point of 30°–32° C.

Example P2
1-(6-Methoxy-1,2-benzisoxazol-3-yl)ethanone (compound 1.2 in Table 1)

In general accordance with the procedure described in Example P1, starting from 1-(2-hydroxy-4-methoxyphenyl)-1-propanone, to give 1-(6-methoxy-1,2-benzisoxazol-3-yl)ethanone having a melting point of 64°–67° C.

Example P3
1-(5-Methoxy-1,2-benzisoxazol-3-yl)ethanone (compound 1.9 in Table 1)

In general accordance with the procedure described in Example P1, starting from 1-(2-hydroxy-5-methoxyphenyl)-1-propanone, to give 1-(5-methoxy-1,2-benzisoxazol-3-yl)ethanone as an oil.

Example P4
1-(6-[3-Trifluoromethylbenzyloxy]-1,2-benzisoxazol-3-yl)ethanone (compound 1.4 in Table 1)

a) 350 ml of a 48% solution of hydrobromic acid are added to 34.2 g of 1-(6-methoxy-1,2-benzisoxazol-3-yl)ethanone in 350 ml of acetic acid. The reaction mixture is refluxed for 6.5 h, cooled, and then poured onto a mixture of ice/water. The precipitated crude product is isolated by filtration and washed with water. This crude product is purified by chromatography over silica gel with ethyl acetate/hexane (1:3), giving 1-(6-hydroxy-1,2-benzisoxazol-3-yl)ethanone having a melting point of 159°–161° C.

b) 2 g of 1-(6-hydroxy-1,2-benzisoxazol-3-yl)ethanone are dissolved in 20 ml of acetone, 2.1 g of potassium carbonate are added and then 3 g of 1-(bromomethyl)-3-(trifluoromethyl)benzene are added dropwise. The reaction mixture is then refluxed for 1 h. After cooling and filtration and concentrating the filtrate under vacuum, the crude product is taken up in ethyl acetate, the organic phase is washed once with water and once with a saturated solution of sodium chloride, dried over sodium sulfate and concentrated. Recrystallistion from ethyl acetate/hexane gives 1-(6-[3-(trifluoromethyl)benzyloxy]-1,2-benzisoxazol-3-yl)ethanone having a melting point of 130°–132° C.

Example P5

The other compounds listed in Tables 1 and 2 can also be prepared in general accordance with the procedures described in Examples P1 to P4 (cProp denotes cyclopropyl). The figures in the column "Phys. Data" denote the melting point.

TABLE 1

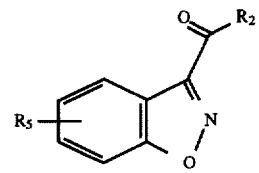

| Compound | $R_2$ | $R_5$ | Phys. data |
|---|---|---|---|
| 1.1 | $CH_3$ | H | 30–32° |
| 1.2 | $CH_3$ | 6-$OCH_3$ | 64–67° C. |
| 1.3 | $CH_3$ | 6-$OCH_2$(cProp-$Cl_2$(2,2)) | resin |
| 1.4 | $CH_3$ | 6-$OCH_2C_6H_4CF_3$(3) | 130–132° C. |
| 1.5 | $CH_3$ | 6-$OCH_2CH=CH_2$ | 121–123° C. |
| 1.6 | $CH_3$ | 6-$OCH_2C\equiv CH$ | 122–123° C. |
| 1.7 | $CH_3$ | 6-$OCH_2C_6H_4CF_3$(4) | 142–146° C. |
| 1.8 | $CH_3$ | 6-$OCH_2C_6H_4CF_3$(2) | 100–102° C. |
| 1.9 | $CH_3$ | 5-$OCH_3$ | oil |
| 1.10 | $CH_3$ | 6-$OCH_2CH=CCl_2$ | 93–95° C. |
| 1.11 | $CH_3$ | 6-$OCF_2CHFCF_3$ | oil |
| 1.12 | $CH_3$ | 4-F | |
| 1.13 | $CH_3$ | 5-F | 50–51° C. |
| 1.14 | $CH_3$ | 6-F | |
| 1.15 | $CH_3$ | 7-F | |
| 1.16 | $CH_3$ | 4-Cl | |
| 1.17 | $CH_3$ | 5-Cl | 55° C. |
| 1.18 | $CH_3$ | 6-Cl | |
| 1.19 | $CH_3$ | 7-Cl | |
| 1.20 | $CH_3$ | 4-$CH_3$ | |
| 1.21 | $CH_3$ | 5-$CH_3$ | |
| 1.22 | $CH_3$ | 6-$CH_3$ | |
| 1.23 | $CH_3$ | 7-$CH_3$ | |
| 1.24 | $CH_3$ | 4-$CF_3$ | |
| 1.25 | $CH_3$ | 5-$CF_3$ | 41° C. |
| 1.26 | $CH_3$ | 6-$CF_3$ | 87° C. |
| 1.27 | $CH_3$ | 7-$CF_3$ | |
| 1.28 | $CH_3$ | 6-$OCF_2CHF_2$ | |
| 1.29 | $CH_3$ | 6-$OCF_2CHFCl$ | |
| 1.30 | $CH_3$ | 6-$OCF_2CHFBr$ | |
| 1.31 | $CH_3$ | 6-$OCHF_2$ | |
| 1.32 | $CH_3$ | 6-$OCF_2Br$ | |
| 1.33 | $CH_3$ | 6-$OCF_3$ | |
| 1.34 | $CH_3$ | 6-$OCH_2$(cProp-$Br_2$(2,2)) | |
| 1.35 | $CH_3$ | 6-$OCH_2$(cProp-$CH_3$(1)-$F_2$(2,2)) | |
| 1.36 | $CH_3$ | 6-$OCH_2C(CH_3)=CH_2$ | |
| 1.37 | $CH_3$ | 6-$OCH_2CH_3$ | |
| 1.38 | $CH_3$ | 6-$OCH_2CH_2CH_3$ | |
| 1.39 | $CH_3$ | 6-$OCH_2CH_2CH_2CH_3$ | |
| 1.40 | $CH_3$ | 6-$OCH_2C_6H_5$ | |
| 1.41 | $CH_3$ | 6-$OCH_2C_6H_4F$(2) | |
| 1.42 | $CH_3$ | 6-$OCH_2C_6H_4F$(3) | |
| 1.43 | $CH_3$ | 6-$OCH_2C_6H_4F$(4) | |
| 1.44 | $CH_3$ | 6-$OCH_2C_6H_4Cl$(2) | |
| 1.45 | $CH_3$ | 6-$OCH_2C_6H_4Cl$(3) | |
| 1.46 | $CH_3$ | 6-$OCH_2C_6H_4Cl$(4) | |
| 1.47 | $CH_3$ | 6-$OCH_2C_6H_4Br$(4) | |
| 1.48 | $CH_3$ | 6-$OCH_2C_6H_4OCH_3$(4) | |
| 1.49 | $CH_3$ | 6-$OCH_2C_6H_3F_2$(2,6) | |
| 1.50 | $CH_3$ | 6-$OCH_2C_6H_3F_2$(2,4) | |
| 1.51 | $CH_3$ | 6-$OCH_2C_6H_3F_2$(3,4) | |
| 1.52 | $CH_3$ | 6-$OCH_2C_6H_3Cl_2$(2,6) | |
| 1.53 | $CH_3$ | 6-$OCH_2C_6H_3Cl_2$(2,4) | |
| 1.54 | $CH_3$ | 6-$OCH_2C_6H_3Cl_2$(3,4) | |
| 1.55 | $CH_3$ | 6-$OC_6H_5$ | |
| 1.56 | $CH_3$ | 6-$OC_6H_4Cl$(4) | |
| 1.57 | $CH_3$ | 6-$OC_6H_4F$(4) | |
| 1.58 | $CH_3$ | 6-$OC_6H_4CN$(4) | |
| 1.59 | $CH_3$ | 6-$OC_6H_4OCH_3$(4) | |
| 1.60 | $CH_3$ | 6-$OC_6H_4CF_3$(4) | |
| 1.61 | $C_2H_5$ | H | |
| 1.62 | $C_2H_5$ | 6-$OCH_2$(cProp-$Cl_2$(2,2)) | |
| 1.63 | $C_2H_5$ | 6-$OCH_2C_6H_4F$(4) | |
| 1.64 | cProp | H | |
| 1.65 | cProp | 6-$OCH_2$(cProp-$Cl_2$(2,2)) | |
| 1.66 | cProp | 6-$OCH_2C_6H_4F$(4) | |
| 1.67 | CN | H | |
| 1.68 | CN | 6-$OCH_2$(cProp-$Cl_2$(2,2)) | |
| 1.69 | CN | 6-$OCH_2C_6H_4F$(4) | |
| 1.70 | CN | 6-$OCH_2C_6H_4CF_3$(3) | |
| 1.71 | CN | 6-$OCF_2CHFCF_3$ | |
| 1.72 | CN | 6-$OCH_2CH=CCl_2$ | |
| 1.73 | $SCH_3$ | H | |
| 1.74 | $CF_3$ | H | |
| 1.75 | $CH_3$ | 6-tert-butyl | oil |

TABLE 2

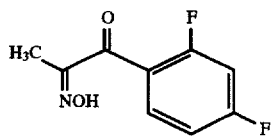

| Compound | R₅ | R₆ | Phys. data |
|---|---|---|---|
| 2.1 | Cl | CH₃ | 159–161° C. |
| 2.2 | Cl | CH₂(cProp-Cl₂(2,2)) | 116–118° C. |
| 2.3 | Cl | CH₂C₆H₄F(4) | |
| 2.4 | Cl | CH₂C₆H₄Cl(4) | |
| 2.5 | Cl | CH₂C₆H₄CF₃(4) | |
| 2.6 | Cl | CH₂C₆H₄CF₃(3) | 141–143° C. |
| 2.7 | Cl | CH₂C₆H₄CF₃(2) | |
| 2.8 | Cl | CF₂CHFCF₃ | 57–59° C. |
| 2.9 | Cl | CF₂CHF₂ | |
| 2.10 | Cl | CHF₂ | |
| 2.11 | Cl | CF₃ | |
| 2.12 | Br | CH₃ | |
| 2.13 | Br | CH₂(cProp-Cl₂(2,2)) | |
| 2.14 | Br | CH₂C₆H₄F(4) | |
| 2.15 | Br | CH₂C₆H₄Cl(4) | |
| 2.16 | Br | CH₂C₆H₄CF₃(4) | |
| 2.17 | Br | CH₂C₆H₄CF₃(3) | |
| 2.18 | Br | CH₂C₆H₄CF₃(2) | |
| 2.19 | Br | CF₂CHFCF₃ | |
| 2.20 | Br | CF₂CHF₂ | |
| 2.21 | Br | CHF₂ | |
| 2.22 | Br | CF₃ | |

Example P6

Methyl 2-[[[(1-{1,2-benzisoxazol-3-yl}ethylidene)amino]oxy]methyl]-α-(methoxymethylene)phenylacetate (compound 3.1 in Table 3)

a) A mixture of 1.4 g of 1-(1,2-benzisoxazol-3-yl)ethanone. 0.7 g of hydroxylamine hydrochloride and 10 ml of pyridine is refluxed for 1 h. The reaction mixture is then poured onto a mixture of ice/water and the precipitated product is isolated by filtration. The product is dissolved in ethyl acetate, the solution is washed once with water, then twice with a saturated solution of sodium chloride and finally dried over sodium sulfate. The solvent is stripped off under vacuum, to give pure 1-(1,2-benzisoxazol-3-yl)ethanone oxime having a melting point of 193°–195° C.

b) A mixture of 0.8 g of 1-(1,2-benzisoxazol-3-yl)ethanone oxime, 1.3 g of methyl 2-(bromomethyl)-α-(methoxymethylene)phenylacetate and 1 g of potassium carbonate in 15 ml of acetonitrile is refluxed for 4 h. The reaction mixture is cooled and filtered and the filtrate is concentrated under vacuum. The residue is dissolved in ethyl acetate and the solution is washed twice with water and once with a saturated solution of sodium chloride and dried over sodium sulfate. After removal of the solvent under vacuum, the residue is purified by chromatography on silica gel with ethyl acetate/hexane (1:3), giving the title compound having a melting point of 97°–98° C.

Example P7 a) Process for the preparation of the intermediate

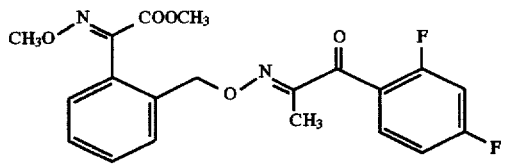

1-(2,4-Difluorophenyl)-propane-1,2-dione-2-oxime 250 ml of a saturated solution of HCl in alcohol are added to a solution of 51.05 g of 2,4-difluoropropiophenone and 36 ml of tert-butyl nitrite in 30 ml of ethanol over 10 minutes at 5° C. The reaction mixture is then stirred for 4 hours at room temperature. The yellow solution is concentrated on a rotary evaporator, tert-butanol is removed azeotropically by adding toluene twice, and the oily residue is crystallised by adition of 300 ml of hexane. Recrystallisation from toluene gives the title compound of m.p. 93°–95° C.

b) Preparation of

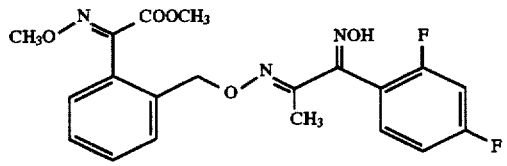

2.07 g of potassium carbonate are added to a solution of 2.86 g of methyl 2-(2-bromomethylphenyl)glyoxylate O-methyloxime and 1.99 g of the ketoxime of a) in 15 ml of acetonitrile, and the mixture is stirred over night at room temperature. Aftewrwards the suspension is stirred into 100 ml of water, followed by extraction with 3×80 ml of ethyl acetate. The combined organic phases are washed with 2×50 ml of water, dried over magnesium sulfate, filtered, and concentrated on a rotary evaporator. The dark oil is chromatographed on silica gel with hexane/ethyl acetate (8:2). Crystallisation from isopropanol gives the pure final product of m.p. 68° C.

c) Preparation of

A suspension of 4.04 g of the keto compound of b) in 35 ml of ethanol is warmed to 35° C. To the resultant colourless solution are added 1.04 g of hydroxylamine hydrochloride and 1.19 g of pyridine. The solution is kept for 5 hours at room temperature and then overnight at 80° C. After concentration on a rotary evaporator, the residue is stirred into 100 ml of water, followed by extraction with 2×80 ml of ethyl acetate. The combined organic phases are dried over magnesium sulfate, filtered and concentrated. Chromatography of the residue over silica gel with hexane/ethyl acetate (8:2) gives the final product in solid form. Recrystallisation from MTBE/hexane gives crystals of m.p. 141° C. [MTBE= methyl tert-butyl ether].

d) Preparation of

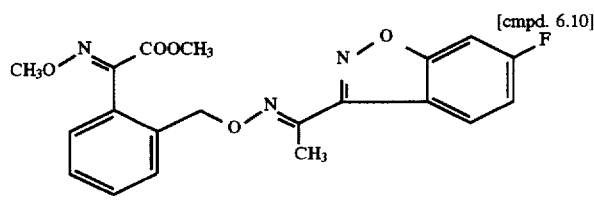
[cmpd. 6.10]

With stirring, 70 mg of potassium hydroxide are added to the colourless solution of 0.42 g of the oxime of c) in 2.6 ml of methanol. The yellowish solution is heated for 45 minutes to reflux. The cooled reaction mixture is then chromatographed direct over 100 g of silica gel with hexane/ethyl acetate (7:3), affording white crystals of the desired product of m.p. 121° C.

Example P8 a) Preparation of

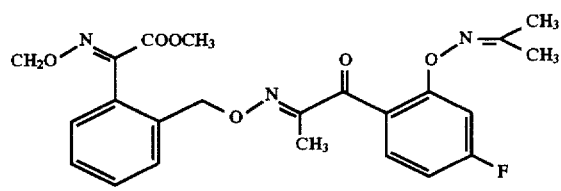

0.48 g of acetone oxime sodium salt is added all at once at room temperature to a solution of 2.02 g of the keto compound of Example P7b) in 5 ml of dimethyl formamide. In the ensuing exothermic reaction the temperature rises to c. 50° C. and the the reaction mixture darkens. The reaction mixture is stirred for 10 minutes, then stirred into 100 ml of ice/water, followed by extraction with 3×50 ml of ethyl acetate. The combined organic phases are concentrated on a rotary evaporator and chromatographed over silica gel with hexane/ethyl acetate (8:2). Crystallisation from MTBE/hexane gives white crystals of the title compound of m.p. 83° C.

b) Preparation of compound 6.10

0.3 ml of conc. hydrochloric acid is added to a solution of 0.114 g of the keto compound of a) in 1 ml of ethanol. The mixture is first refluxed for 3 hours and then allowed to stand for 2 ½ days at room temperature. The white solid obtained is isolated by filtration and dried under a high vacuum to give white crystals of the desired product of m.p. 120° C., which is identical with the product of Example P7d).

Example P9 a) Preparation of 1-(2-fluorophenyl)propane-1,2-dione-2-oxime

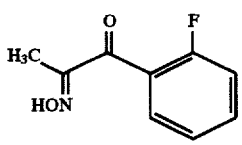
(A)

HCl gas is introduced into 300 ml of dioxane over 1 minute. Then 30.4 g (0.2 mol) of 2-fluoropropiophenone are dissolved in this solution and afterwards 28.3 g (0.24 mol) of isopentyl nitrite are added dropwise. The reaction mixture is stirred for 30 hours at room temperature and then made alkaline with with triethylamine. The reaction mixture is concentrated, the residue is taken up in ethyl acetate, washed twice with water and once with a saturated solution of sodium chloride, dried over sodium sulfate and concentrated under vacuum. The crude product is recrystallised from hexane, affording 20.3 g of the title compound of m.p. 72°–74° C.

b) Preparation of 1-(2-fluorophenyl)propane-1,2-dione-dioxime

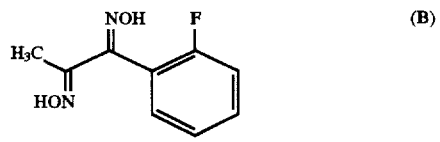
(B)

A mixture of 5.4 g of (A) (0.03 mol), 2.15 g (0.031 mol) of hydroxylammonium chloride, 2.4 g (0.03 mol) of pyridine and 30 ml of ethanol is refluxed for 2 hours. The reaction mixture is concentrated under vacuum and 100 ml of water are added. The precipitated product is isolated by filtration, washed repeatedly with water and dried under vacuum, affording compound (B). m.p. 255°–256° C.

c) Preparation of 1-benzo[d]isoxazol-3-yl-ethanone oxime

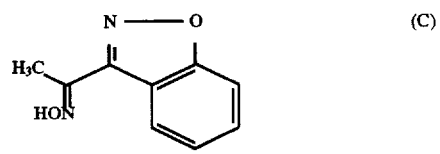
(C)

1.7 g (8.7 mmol) of (B), 0.6 g (8.7 mmol) of potassium hydroxide and 40 ml of ethanol are refluxed for 1 hour. Then a further 0.6 g (8.7 mol) of potassium hydroxide is added to the reaction mixture, which is further refluxed for ½ hour. The reaction mixture is cooled, diluted with water, and acidified with a 10% solution of HCl. After extraction with ethyl acetate the organic phase is washed 3 times with water, once with a saturated solution of sodium chloride, dried over sodium sulfate and concentrated under vacuum. The product is suspended in hexane, isolated by filtration, and dried, affording compound (C), m.p. 195–197° C.

The other compounds listed in Tables 3 to 7 can also be prepared in general accordance with the procedures described in Examples P6 to P9 (cProp denotes cyclopropyl). The figures in the column "Phys. Data" denote the melting point. Where indicated, the letters A and B each denote E/Z isomers.

TABLE 3

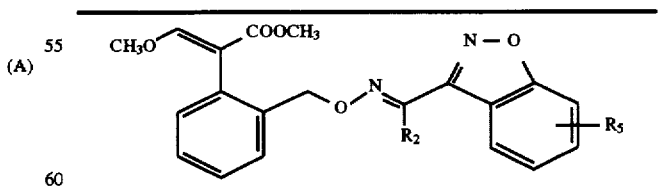

| Compound | R₂ | R₅ | Phys. data |
|---|---|---|---|
| 3.1 | CH₃ | H | 97–98° C. |
| 3.2 | CH₃ | 6-OCH₃ | 113–115° C. |
| 3.3 | CH₃ | 6-OCH₂(cProp-Cl₂(2,2)) | 113–116° C. |
| 3.4 | CH₃ | 6-OCH₂C₆H₄CF₃(3) | 138–140° C. |
| 3.5 | CH₃ | 6-OCH₂CH=CH₂ | 97–101° C. |

TABLE 3-continued

[Structure: CH3O, COOCH3, N—O, R5 substituted benzisoxazole]

| Compound | R₂ | R₅ | Phys. data |
|---|---|---|---|
| 3.6 | CH₃ | 6-OCH₂C≡CH | 127–130° C. |
| 3.7 | CH₃ | 6-OCH₂C₆H₄CF₃(4) | 143–147° C. |
| 3.8 | CH₃ | 6-OCH₂C₆H₄CF₃(2) | 128–131° C. |
| 3.9 | CH₃ | 5-OCH₃ | 125–127° C. |
| 3.10 | CH₃ | 6-OCH₂CH=CCl₂ | 127–129° C. |
| 3.11A | CH₃ | 6-OCF₂CHFCF₃ | oil |
| 3.11B | CH₃ | 6-OCF₂CHFCF₃ | oil |
| 3.12 | CH₃ | 4-F | 94° C. |
| 3.13 | CH₃ | 5-F | 128–129° C. |
| 3.14 | CH₃ | 6-F | 139° C. |
| 3.15 | CH₃ | 7-F | 112° C. |
| 3.16 | CH₃ | 4-Cl | |
| 3.17 | CH₃ | 5-Cl | 133–134° C. |
| 3.18 | CH₃ | 6-Cl | |
| 3.19 | CH₃ | 7-Cl | |
| 3.20 | CH₃ | 4-CH₃ | |
| 3.21 | CH₃ | 5-CH₃ | |
| 3.22 | CH₃ | 6-CH₃ | |
| 3.23 | CH₃ | 7-CH₃ | |
| 3.24 | CH₃ | 4-CF₃ | |
| 3.25 | CH₃ | 5-CF₃ | 127–128° C. |
| 3.26A | CH₃ | 6-CF₃ | 102° C. |
| 3.26B | CH₃ | 6-CF₃ | 86° C. |
| 3.27 | CH₃ | 7-CF₃ | |
| 3.28 | CH₃ | 6-OCF₂CHF₂ | 97–98° C. |
| 3.29 | CH₃ | 6-OCF₂CHFCl | |
| 3.30 | CH₃ | 6-OCF₂CHFBr | |
| 3.31 | CH₃ | 6-OCHF₂ | |
| 3.32 | CH₃ | 6-OCF₂Br | |
| 3.33 | CH₃ | 6-OCF₃ | |
| 3.34 | CH₃ | 6-OCH₂(cProp-Br₂(2,2)) | |
| 3.35 | CH₃ | 6-OCH₂(cProp-CH₃(1)-F₂(2,2)) | |
| 3.36 | CH₃ | 6-OCH₂C(CH₃)=CH₂ | |
| 3.37 | CH₃ | 6-OCH₂CH₃ | |
| 3.38 | CH₃ | 6-OCH₂CH₂CH₃ | |
| 3.39 | CH₃ | 6-OCH₂CH₂CH₂CH₃ | |
| 3.40 | CH₃ | 6-OCH₂C₆H₅ | |
| 3.41 | CH₃ | 6-OCH₂C₆H₄F(2) | 121–124° C. |
| 3.42 | CH₃ | 6-OCH₂C₆H₄F(3) | 121–124° C. |
| 3.43 | CH₃ | 6-OCH₂C₆H₄F(4) | 119–121° C. |
| 3.44 | CH₃ | 6-OCH₂C₆H₄Cl(2) | |
| 3.45 | CH₃ | 6-OCH₂C₆H₄Cl(3) | |
| 3.46 | CH₃ | 6-OCH₂C₆H₄Cl(4) | |
| 3.47 | CH₃ | 6-OCH₂C₆H₄Br(4) | |
| 3.48 | CH₃ | 6-OCH₂C₆H₄OCH₃(4) | |
| 3.49 | CH₃ | 6-OCH₂C₆H₃F₂(2,6) | |
| 3.50 | CH₃ | 6-OCH₂C₆H₃F₂(2,4) | |
| 3.51 | CH₃ | 6-OCH₂C₆H₃F₂(3,4) | |
| 3.52 | CH₃ | 6-OCH₂C₆H₃Cl₂(2,6) | |
| 3.53 | CH₃ | 6-OCH₂C₆H₃Cl₂(2,4) | |
| 3.54 | CH₃ | 6-OCH₂C₆H₃Cl₂(3,4) | |
| 3.55 | CH₃ | 6-OC₆H₅ | |
| 3.56 | CH₃ | 6-OC₆H₄Cl(4) | |
| 3.57 | CH₃ | 6-OC₆H₄F(4) | |
| 3.58 | CH₃ | 6-OC₆H₄CN(4) | |
| 3.59 | CH₃ | 6-OC₆H₄OCH₃(4) | |
| 3.60 | CH₃ | 6-OC₆H₄CF₃(4) | |
| 3.61 | C₂H₅ | H | |
| 3.62 | C₂H₅ | 6-OCH₂(cProp-Cl₂(2,2)) | |
| 3.63 | C₂H₅ | 6-OCH₂C₆H₄F(4) | |
| 3.64 | cProp | H | |
| 3.65 | cProp | 6-OCH₂(cProp-Cl₂(2,2)) | |
| 3.66 | cProp | 6-OCH₂C₆H₄F(4) | |
| 3.67 | CN | H | |
| 3.68 | CN | 6-OCH₂(cProp-Cl₂(2,2)) | |
| 3.69 | CN | 6-OCH₂C₆H₄F(4) | |
| 3.70 | CN | 6-OCH₂C₆H₄CF₃(3) | |
| 3.71 | CN | 6-OCF₂CHFCF₃ | |
| 3.72 | CN | 6-OCH₂CH=CCl₂ | |
| 3.73 | SCH₃ | H | |
| 3.74 | CF₃ | H | |
| 3.75 | CH₃ | 6-OCH₂C₆H₃(CF₃)₂(3,5) | 148–150° C. |
| 3.76 | CH₃ | 6-OCH₂C₆H₄(t.But.)(4) | 120–122° C. |
| 3.77 | CH₃ | 6-t.Butyl | 129–131° C. |
| 3.78 | CH₃ | 6-OC₂H₅ | 114–116° C. |
| 3.79 | CH₃ | 6-OisoC₃H₇ | |
| 3.80 | CH₃ | 6-Osek.C₄H₉ | |
| 3.81 | CH₃ | 6-OC₃H₇(n) | |
| 3.82 | CH₃ | 6-OC₄H₉(iso) | |

TABLE 4

[Structure: CH3O, COOCH3, N—O, benzisoxazole with R5 and O-R6 substituents]

| Compound | R₅ | R₆ | Phys. data |
|---|---|---|---|
| 4.1 | Cl | CH₃ | 175–176° C. |
| 4.2 | Cl | CH₂(cProp-Cl₂(2,2)) | 130–131° C. |
| 4.3 | Cl | CH₂C₆H₄F(4) | |
| 4.4 | Cl | CH₂C₆H₄Cl(4) | |
| 4.5 | Cl | CH₂C₆H₄CF₃(4) | |
| 4.6 | Cl | CH₂C₆H₄CF₃(3) | 170–171° C. |
| 4.7 | Cl | CH₂C₆H₄CF₃(2) | |
| 4.8 | Cl | CF₂CHFCF₃ | 107–109° C. |
| 4.9 | Cl | CF₂CHF₂ | |
| 4.10 | Cl | CHF₂ | |
| 4.11 | Cl | CF₃ | |
| 4.12 | Br | CH₃ | |
| 4.13 | Br | CH₂(cProp-Cl₂(2,2)) | |
| 4.14 | Br | CH₂C₆H₄F(4) | |
| 4.15 | Br | CH₂C₆H₄Cl(4) | |
| 4.16 | Br | CH₂C₆H₄CF₃(4) | |
| 4.17 | Br | CH₂C₆H₄CF₃(3) | |
| 4.18 | Br | CH₂C₆H₄CF₃(2) | |
| 4.19 | Br | CF₂CHFCF₃ | |
| 4.20 | Br | CF₂CHF₂ | |
| 4.21 | Br | CHF₂ | |
| 4.22 | Br | CF₃ | |
| 4.23 | F | CH₂C₆H₄F(4) | 96–100° C. |
| 4.24 | F | CH₂C₆H₄CF₃(4) | 125–128° C. |
| 4.25 | F | CH₂(cProp-Cl₂(2,2)) | 131–134° C. |

TABLE 5

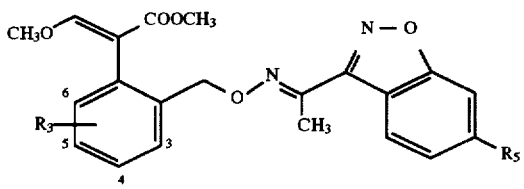

| Compound | R₃ | R₅ | Phys. data |
|---|---|---|---|
| 5.1 | 3-Cl | H | |
| 5.2 | 3-Cl | OCH₃ | |
| 5.3 | 3-Cl | OCH₂(cProp-Cl₂(2,2)) | |
| 5.4 | 3-Cl | OCH₂C₆H₄CF₃(3) | |
| 5.5 | 3-Cl | OCH₂C₆H₄F(4) | |
| 5.6 | 3-Cl | OCH₂CH=CF₂ | |
| 5.7 | 3-Cl | OCF₂CHFCF₃ | |
| 5.8 | 4-Cl | H | |
| 5.9 | 4-Cl | OCH₃ | |
| 5.10 | 4-Cl | OCH₂(cProp-Cl₂(2,2)) | |
| 5.11 | 4-Cl | OCH₂C₆H₄CF₃(3) | |
| 5.12 | 4-Cl | OCH₂C₆H₄F(4) | |
| 5.13 | 4-Cl | OCH₂CH=CF₂ | |
| 5.14 | 4-Cl | OCF₂CHFCF₃ | |
| 5.15 | 5-Cl | H | |
| 5.16 | 5-Cl | OCH₃ | |
| 5.17 | 5-Cl | OCH₂(cProp-Cl₂(2,2)) | |
| 5.18 | 5-Cl | OCH₂C₆H₄CF₃(3) | |
| 5.19 | 5-Cl | OCH₂C₆H₄F(4) | |
| 5.20 | 5-Cl | OCH₂CH=CF₂ | |
| 5.21 | 5-Cl | OCF₂CHFCF₃ | |
| 5.22 | 6-Cl | H | |
| 5.23 | 6-Cl | OCH₃ | |
| 5.24 | 6-Cl | OCH₂(cProp-Cl₂(2,2)) | |
| 5.25 | 6-Cl | OCH₂C₆H₄CF₃(3) | |
| 5.26 | 6-Cl | OCH₂C₆H₄F(4) | |
| 5.27 | 6-Cl | OCH₂CH=CF₂ | |
| 5.28 | 6-Cl | OCF₂CHFCF₃ | |
| 5.29 | 4-F | H | |
| 5.30 | 4-F | OCH₃ | |
| 5.31 | 4-F | OCH₂(cProp-Cl₂(2,2)) | |
| 5.32 | 4-F | OCH₂C₆H₄CF₃(3) | |
| 5.33 | 4-F | OCH₂C₆H₄F(4) | |
| 5.34 | 4-F | OCH₂CH=CF₂ | |
| 5.35 | 4-F | OCF₂CHFCF₃ | |
| 5.36 | 4-OCH₃ | H | |
| 5.37 | 4-OCH₃ | OCH₃ | |
| 5.38 | 4-OCH₃ | OCH₂(cProp-Cl₂(2,2)) | |
| 5.39 | 4-OCH₃ | OCH₂C₆H₄CF₃(3) | |
| 5.40 | 4-OCH₃ | OCH₂C₆H₄F(4) | |
| 5.41 | 4-OCH₃ | OCH₂CH=CF₂ | |
| 5.42 | 4-OCH₃ | OCF₂CHFCF₃ | |
| 5.43 | 3-CH₃ | H | |
| 5.44 | 3-CH₃ | OCH₃ | |
| 5.45 | 3-CH₃ | OCH₂(cProp-Cl₂(2,2)) | |
| 5.46 | 3-CH₃ | OCH₂C₆H₄CF₃(3) | |
| 5.47 | 3-CH₃ | OCH₂C₆H₄F(4) | |
| 5.48 | 3-CH₃ | OCH₂CH=CF₂ | |
| 5.49 | 3-CH₃ | OCF₂CHFCF₃ | |
| 5.50 | 6-CH₃ | H | |
| 5.51 | 6-CH₃ | OCH₃ | |
| 5.52 | 6-CH₃ | OCH₂(cProp-Cl₂(2,2)) | |
| 5.53 | 6-CH₃ | OCH₂C₆H₄CF₃(3) | |
| 5.54 | 6-CH₃ | OCH₂C₆H₄F(4) | |
| 5.55 | 6-CH₃ | OCH₂CH=CF₂ | |
| 5.56 | 6-CH₃ | OCF₂CHFCF₃ | |

TABLE 6

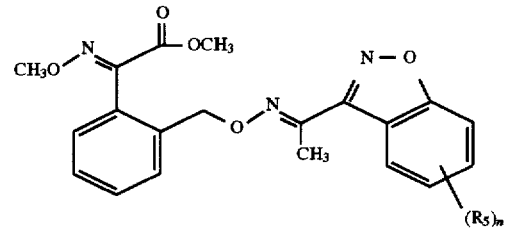

| Compound | (R₅)ₙ | Phys. data |
|---|---|---|
| 6.1 | H | 106–108° C. |
| 6.2 | 6-OCH₃ | |
| 6.3 | 6-OCH₂CH=CH₂ | |
| 6.4 | 6-OCF₃ | |
| 6.5 | 6-OCHF₂ | |
| 6.6 | 6-OCF₂Cl | |
| 6.7 | 6-OCF₂Br | |
| 6.8 | 4-F | 113° C. |
| 6.9 | 5-F | 168–169° C. |
| 6.10 | 6-F | 121° C. |
| 6.11 | 7-F | 105° C. |
| 6.12 | 4-Cl | |
| 6.13 | 5-Cl | |
| 6.14 | 6-Cl | |
| 6.15 | 7-Cl | |
| 6.16 | 4-Me | |
| 6.17 | 5-Me | |
| 6.18 | 6-Me | |
| 6.19 | 7-Me | |
| 6.20 | 6-t-butyl | |
| 6.21 | 6-cyclopropyl | |
| 6.22 | 6-phenyl | |
| 6.23 | 5,6-Cl₂ | |
| 6.24 | 5-F,6-OMe | |
| 6.25 | 5-Cl,6-OMe | |
| 6.26 | 5,7-Me₂ | |
| 6.27 | 4-CF₃ | |
| 6.28 | 5-CF₃ | oil (E/Z mixture) |
| 6.29 | 6-CF₃ | 96° C. |
| 6.30 | 7-CF₃ | |
| 6.31 | 6-OC₂H₅ | |
| 6.32 | 6-OC₃H₇(n) | |
| 6.33 | 6-OC₄H₉(n) | |
| 6.34 | 6-OC₄H₉(sec) | |

TABLE 7

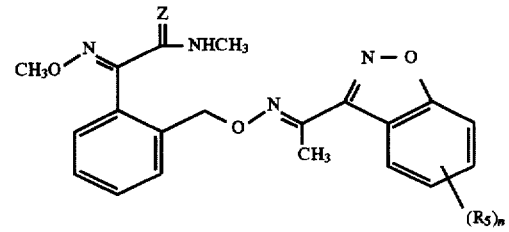

| Compound | Z | (R₅)ₙ | Phys. data |
|---|---|---|---|
| 7.1 | O | H | 128° C. |
| 7.2 | S | H | 141° C. |
| 7.3 | S=O | H | 162° C. |
| 7.4 | O | 6-OCH₃ | |
| 7.5 | S | 6-OCH₃ | |
| 7.6 | O | 6-OCH₂CH=CH₂ | |
| 7.7 | S | 6-OCH₂CH=CH₂ | |
| 7.8 | O | 6-OCF₃ | |
| 7.9 | S | 6-OCF₃ | |
| 7.10 | O | 6-OCHF₂ | |
| 7.11 | S | 6-OCHF₂ | |
| 7.12 | O | 6-OCF₂Br | |

TABLE 7-continued

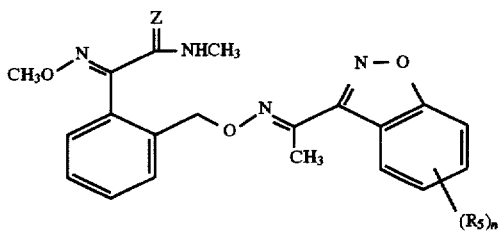

| Compound | Z | (R₅)ₙ | Phys. data |
|---|---|---|---|
| 7.13 | S | 6-OCF₂Br | |
| 7.14 | O | 6-OCF₂Cl | |
| 7.15 | S | 6-OCF₂Cl | |
| 7.16 | O | 4-F | 126° C. |
| 7.17 | S | 4-F | |
| 7.18 | O | 5-F | 158–160° C. |
| 7.19 | S | 5-F | 133-134° C. |
| 7.20 | S=O | 5-F | |
| 7.21 | O | 6-F | 145° C. |
| 7.22 | S | 6-F | 118° C. |
| 7.23 | S=O | 6-F | |
| 7.24 | O | 7-F | 136° C. |
| 7.25 | S | 7-F | 103° C. |
| 7.26 | O | 4-Cl | |
| 7.27 | S | 4-Cl | |
| 7.28 | O | 5-Cl | 156-158° C. |
| 7.29 | S | 5-Cl | 121-122° C. |
| 7.30 | S=O | 5-Cl | |
| 7.31 | O | 6-Cl | |
| 7.32 | S | 6-Cl | |
| 7.33 | S=O | 6-Cl | |
| 7.34 | O | 7-Cl | |
| 7.35 | S | 7-Cl | |
| 7.36 | O | 4-CH₃ | |
| 7.37 | S | 4-CH₃ | |
| 7.38 | O | 5-CH₃ | |
| 7.39 | S | 5-CH₃ | |
| 7.40 | O | 6-CH₃ | |
| 7.41 | S | 6-CH₃ | |
| 7.42 | O | 7-CH₃ | |
| 7.43 | S | 7-CH₃ | |
| 7.44 | O | 6-t-butyl | |
| 7.45 | S | 6-6-butyl | |
| 7.46 | O | 6-cyclopropyl | |
| 7.47 | S | 6-cyclopropyl | |
| 7.48 | O | 6-phenyl | |
| 7.49 | S | 6-phenyl | |
| 7.50 | O | 5,6-Cl₂ | |
| 7.51 | S | 5,6-Cl₂ | |
| 7.52 | O | 5-F,6-OMe | |
| 7.53 | S | 5-F,6-OMe | |
| 7.54 | O | 5-Cl,6-OMe | |
| 7.55 | S | 5-Cl,6-OMe | |
| 7.56 | O | 5,7-(CH₃)₂ | |
| 7.57 | S | 5,7-(CH₃)₂ | |
| 7.58 | O | 4-CF₃ | |
| 7.59 | S | 4-CF₃ | |
| 7.60 | O | 5-CF₃ | 121–122° C. (E,Z isomer) |
| 7.61 | O | 5-CF₃ | 185° C. (E,E isomer) |
| 7.62 | S | 5-CF₃ | 136° C. (E,Z isomer) |
| 7.63 | S | 5-CF₃ | 98–100° C. (E,E isomer) |
| 7.64 | S=O | 5-CF₃ | |
| 7.65 | O | 6-CF₃ | 143° C. |
| 7.66 | S | 6-CF₃ | 130° C. |
| 7.67 | S=O | 6-CF₃ | |
| 7.68 | O | 7-CF₃ | |
| 7.69 | S | 7-CF₃ | |
| 7.70 | O | 6-OC₂H₅ | |
| 7.71 | S | 6-OC₂H₅ | |
| 7.72 | O | 6-OC₃H₇(iso) | |
| 7.73 | S | 6-OC₃H₇(iso) | |
| 7.74 | O | 6-OC₄H₉(tert) | |
| 7.75 | S | 6-OC₄H₉(tert) | |
| 7.76 | S=O | 6-OC₃H₇(iso) | |
| 7.77 | O | 6-OC₃H₇(n) | |

TABLE 7-continued

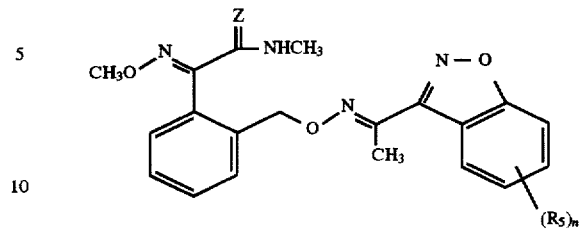

| Compound | Z | (R₅)ₙ | Phys. data |
|---|---|---|---|
| 7.78 | S | 6-OC₃H₇(n) | |
| 7.79 | S=O | 6-OC₃H₇(n) | |
| 7.80 | O | 6-OC₄H₉(sec) | |
| 7.81 | S | 6-OC₄H₉(sec) | |
| 7.82 | S=O | 6-OC₄H₉(sec) | |

Formulation Examples (%=per cent by weight; ratios= weight ratios)

Example F1
Emulsifiable concentrate

| | a) | b) | c) |
|---|---|---|---|
| active ingredient | 25% | 40% | 50% |
| calcium dodecylbenzenesulfonate | 5% | 8% | 6% |
| polyethoxylated castor oil (36 mol EO) | 5% | — | — |
| tributylphenol polyethoxylate (30 mol EO) | — | 12% | 4% |
| cyclohexanone | — | 15% | 20% |
| xylene mixture | 65% | 25% | 20% |

Finely ground active ingredient and adjuvants are mixed to give an emulsifiable concentrate from which emulsions of any desired concentration are obtained by dilution with water.

Example F2
Solutions

| | a) | b) | c) | d) |
|---|---|---|---|---|
| active ingredient | 80% | 10% | 5% | 95% |
| 2-methoxyethanol | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| petroleum spirit (boiling range 160–190° C.) | — | — | 94% | — |

A solution which is suitable for use in the form of microdrops is obtained by mixing finely ground active ingredient and adjuvants.

Example F3
Granulates

| | a) | b) | c) | d) |
|---|---|---|---|---|
| active ingredient | 5% | 10% | 8% | 21% |
| kaolin | 94% | — | 79% | 54% |
| highly dispersed silica | 1% | — | 13% | 7% |
| attapulgite | — | 90% | — | 18% |

The active ingredient is dissolved in dichloromethane, the solution is sprayed on to the carrier, and the solvent is subsequently evaporated in vacuo.

Example F4
Dusts

|  | a) | b) |
|---|---|---|
| active ingredient | 2% | 5% |
| highly dispersed silica | 1% | 5% |
| talcum | 97% | — |
| kaolin | — | 90% |

Ready-to-use dusts are prepared by mixing the active ingredient with the active ingredient

Example F5
Wettable powders

|  | a) | b) | c) |
|---|---|---|---|
| active ingredient | 25% | 50% | 75% |
| sodium ligninsulfonate | 5% | 5% | — |
| sodium lauryl sulfate | 3% | — | 5% |
| sodium diisobutylnaphthalene-sulfonate | — | 6% | 10% |
| octylphenol polyethoxylate (7–8 mol EO) | — | 2% | — |
| highly dispersed silica | 5% | 10% | 10% |
| kaolin | 62% | 27% | — |

The active ingredient are mixed with the additives, and the mixture is ground thoroughly in a suitable mill to give wettable powders from which suspensions of any desired concentration can be obtained by dilution with water.

Example F6
Emulsifiable concentrate

| active ingredient | 10% |
|---|---|
| octylphenoxy polyethoxyethanol (4–5 mol EO) | 3% |
| calcium dodecylbenzenesulfonate | 3% |
| polyethoxylated castor oil (36 mol EO) | 4% |
| cyclohexanone | 30% |
| xylene mixture | 50% |

Finely ground active ingredient and adjuvants are mixed to give an emulsifiable concentrate from which emulsions of any desired concentration can be prepared.

Example F7
Dusts

|  | a) | b) |
|---|---|---|
| combination (1:2) | 5% | 8% |
| talcum | 95% | — |
| kaolin | — | 92% |

Ready-to-use dusts are obtained by mixing the active ingredients with the carrier and grinding the mixture on a suitable mill.

Example F8
Extruder granules

| combination (1:3) | 10% |
|---|---|
| sodium ligninsulfonate | 2% |
| carboxymethyl cellulose | 1% |
| kaolin | 87% |

The active ingredients are mixed with the additives, and the mixture is ground and moistened with water. This mixture is extruded, granulated and subsequently dried in a stream of air.

Example F9
Coated granulates

| combination (1:1) | 3% |
|---|---|
| polyethylene glycol (MW 200) | 3% |
| kaolin | 94% |

In a mixer, the finely ground active ingredients are applied uniformly to the polyethylene glycol, which has been moistened with kaolin, to give dust-free coated granules.

Example F10
Suspension concentrate

| combination (2:1) | 40% |
|---|---|
| ethylene glycol | 10% |
| nonylphenoxy polyethoxyethanol (15 mol EO) | 6% |
| sodium ligninsulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

Finely ground active ingredient and adjuvants are mixed to give a suspension concentrate from which suspensions of any desired concentration are prepared by dilution with water.

BIOLOGICAL EXAMPLES
A) Microbicidal action

Example B1
Action against Phytophthora infestans on tomatoes
a) Curative action After a cultivation period of 3 weeks, tomato plants of the "Roter Gnom" variety are sprayed with a zoospore suspension of the fungus and incubated in a humidity chamber at 18°–20° C. and saturated atmospheric humidity. Wetting is discontinued after 24 hours. After the plants have dried, they are sprayed with a mixture prepared from a wettable powder formulation of the test compound in a concentration of 200 ppm. After the spray coating has dried, the plants are put back into the climatic chamber for 4 days. The number and size of the typical leaf specks occurring after this time serve as indicators for determining the efficacy of the test compounds.

b) Preventive-systemic action

A wettable powder formulation of the test compound is applied in a concentration of 600 ppm (based on the volume of the soil) to the surface of the soil of 3-week-old tomato plants of the "Roter Gnom" variety. After a waiting time of 3 weeks, the underside of the leaves of the plants is sprayed with a zoospore suspension of Phytophthora infestans. The plants are then kept for 5 days in a spray chamber at 18°–20° C. and saturated atmospheric humidity. The number and size of the typical leaf specks occurring after this time serve as indicators for determining the efficacy of the test compounds.

Whereas infestation is 100% on untreated and infected control plants, infestation in both tests is reduced to 20% or less with compounds of Tables 3 to 7, especially with compounds 3.1, 3.2, 3.5, 3.13, 3.17, 3.28, 3.78, 3.82, 7.1, 7.18, 7.28, 7.71.

Example B2

Action against *Plasmopara viticola* (Bert. et Curt.) (Berl. et DeToni) on vines a) Residual preventive action Vine cuttings of the Chasselas variety are reared in a greenhouse. Three plants in the 10-leaf stage are sprayed with a spray mixture formulation (200 ppm a.i.) of the test compound. After the spray coating has dried, the plants are infected uniformly on the underside of the leaves with a spore suspension of the fungus. The plants are then kept in a humidity chamber for 8 days, after which time marked symptoms of disease are observed on the control plants. The number and size of the infected areas on the untreated plants act as an indicator of the efficacy of the tested compounds.

b) Curative action

Vine cuttings of the Chasselas variety are reared in a greenhouse and sprayed in the 10-leaf stage on the underside of the leaves with a spore suspension of *Plasmopara viticola*. After 24 hours in the humidity chamber, the plants are sprayed with a spray mixture (200 ppm) of the test compound. The plants are then kept for another 7 days in the humidity chamber. After this time the control plants exhibit symptoms of the disease. The number and size of the infected areas on the untreated plants act as an indicator of the efficacy of the tested compounds.

Compared with the control plants, infestation on the plants treated with compounds of formula I is 20% or less.

Example B3

Action against *Pythium debaryanum* on sugarbeet (*Beta vulgaris*)

a) Action after soil application

The fungus is cultivated on sterile oat grains and added to a mixture of soil and sand. Flowerpots are filled with the infected soil in which sugarbeet seeds are then sown. Immediately after sowing, an aqueous suspension (20 ppm a.i., based on the volume of the soil) prepared from a wettable powder formulation of the test compound is poured over the soil. The pots are then stood in a greenhouse at 20°–24° C. for 2–3 weeks. The soil is kept uniformly moist by continual light spraying with water. Evaluation of the test is made by observing the emergence of the sugarbeet plants and counting the number of healthy and diseased plants.

b) Action after dressing application

The fungus is cultivated on sterile oat grains and added to a mixture of soil and sand. Flowerpots are filled with the infected soil in which sugarbeet seeds are sown that have been dressed with a dressing powder formulation of the test compound (1000 ppm a.i., based on the weight of the seeds). The pots are then stood in a greenhouse at 20°–24° C. for 2–3 weeks. The soil is kept uniformly moist by lightly spraying it with water. Evaluation of the test is made by observing the emergence of the sugarbeet plants and counting the number of healthy and diseased plants.

After treatment with compounds of formula I, in particular with compounds 3.1, 3.2, 3.5, 3.6, 3.28, 7.1, 7.18, 7.28, 7.71, more than 80% of the plants emerge and have a healthy appearance. In the control pots, only isolated plants of unhealthy appearance are observed.

Example B4

Residual-protective action against *Cercospora arachidicola* on groundnut plants Groundnut plants 10–15 cm in height are sprayed to drip point with an aqueous spray mixture (0.02% a.i.) of the test compound and infected 48 hours later with a conidia suspension of the fungus. The infected plants are incubated for 72 hours at c. 21° C. and high humidity and then stood in a greenhouse until the typical leaf specks occur. Evaluation of the fungicidal action is made 12 days after infection and is based on the number and size of the specks.

Compounds of formula I reduce the leaf specks to below c. 10% of the leaf surface. In some cases, infestation is completely controlled (0–5% infestation).

Example B5

Action against *Puccinia graminis* on wheat a) Residual-protective action

Wheat plants are sprayed to drip point 6 days after sowing with an aqueous spray mixture (0.02% a.i.) of the test compound and infected 24 hours later with a uredospore suspension of the fungus. After an incubation time of 48 hours (conditions: 95–100% relative humidity at 20° C.), the plants are stood at 22° C. in a greenhouse. Evaluation of the rust pustule development is made 12 days after infection.

b) Systemic action

Wheat plants are drenched 5 days after sowing with an aqueous spray mixture of the test compound (0.006% a.i., based on the volume of the soil). Care is taken that the spray mixture does not come in contact with the growing parts of plants. After 48 hours, the plants are infected with a uredospore suspension of the fungus. After an incubation period of 48 hours (conditions: 95–100% relative humidity at 20° C.), the plants are stood at 22° C. in a greenhouse. Evaluation of the rust pustule development is made 12 days after infection (compounds 1.1, 1.3 and others).

Compounds of formula I, especially those of Table 1, in particular compounds 3.1, 3.2, 3.5, 3.13, 3.17, 3.28, 3.78, 3.82, 7.1, 7.18, 7.28, 7.70, 7.76, effect a marked reduction of fungus infestation, in some cases to 10–0%.

Example B6

Action against *Pyricularia oryzae* on rice plants a) Residual-protective action After a cultivation period of 2 weeks, rice plants are sprayed to drip point with an aqueous spray mixture (0.02% a.i.) of the test compound. After 48 hours the treated plants are infected with a conidia suspension of the fungus. Evaluation of fungus attack is made 5 days after infection, while maintaining conditions of 95–100% relative humidity and 22° C.

b) Systemic action 2-week-old rice plants are drenched with a spray mixture of the test compound (0.006% a.i., based on the volume of the soil), while ensuring that the spray mixture does not come in contact with the growing parts of plants. The pots are then filled with water until the lowermost parts of the rice stalks are standing in water. After 96 hours the treated rice plants are infected with a conidia suspension of the fungus. Fungus infestation is evaluated after incubating the infected plants for 5 days at 95–100% relative humidity and c. 24° C. Compounds of formula I substantially inhibit the outbreak of the disease on the infected plants.

Example B7
Residual protective action against *Venturia inaequalis* on apple shoots Apple cuttings with 10–20 cm long fresh shoots are sprayed with a spray mixture (0.02% a.i.) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection. Compounds of formula I of one of Tables 3–7 have a substantially lasting action against scab diseases.

Example B8
Action against *Erysiphe graminis* on barley
a) Residual protective action Barley plants about 8 cm in height are sprayed to drip point with a spray mixture (0.02% a.i.) of the test compound and the treated plants are dusted with conidia of the fungus 3 to 4 hours later. The infected plants are stood in a greenhouse at c. 22° C. and fungus infestation is evaluated 10 days after infection.
b) Systemic action Barley plants about 8 cm in height are drenched with an aqueous spray mixture (0.002% a.i., based on the volume of the soil) of the test compound. Care is taken that the spray mixture does not come in contact with the growing parts of the plants. The treated plants are dusted 48 hours later with conidia of the fungus. The infected plants are then stood in a greenhouse at c. 22° C. and evaluation of infestation is made 10 days after infection. Compounds of formula I of Tables 3–7, in particular compounds 3.1, 3.17, 3.78, 3.82 and 7.76 are substantially able to reduce infestation to less than 10%, and in some cases also almost completely.

Example B9
Action against *Podosphaera leucotricha* on apple shoots
Residual-protective action Apple cuttings with c. 15 cm fresh shoots are sprayed with a spray mixture (0.06% a.i.) of the test compound. The plants are infected 24 hours later with a conidia suspension of the fungus and then stood in a humidity chamber at 70% relative humidity at 20° C. Fungus infestation is evaluated 12 days after infection.

Compounds of formula I inhibit infestation to less than 20%. Infestation of control plants is 100%.

Example B10
Action against *Botrytis cinerea* on apples
Residual-protective action Artificially damaged apples are treated by dropping a spray mixture (0.02% a.i.) of the test compound on to the injury sites. The treated fruit is then inoculated with a spore suspension of the fungus and incubated for 1 week at high humidity and c. 20° C. The fungicidal action of the test compound is determined from the number of injury sites attacked by rot. Compounds of formula I of Tables 3–7 are able to inhibit rot completely.

Example B11
Action against *Helminthosporium gramineum*

Wheat grains are contaminated with a spore suspension of the fungus and left to dry. The contaminated grains are dressed with a suspension of the test compound (600 ppm a.i., based on the weight of the seeds). Two days later the grains are laid out on agar dishes and development of the fungus colonies around the grains is assessed after 4 days. Evaluation of the test compound is made by assessing the number and size of the colonies. Some of the compounds of formula I are very effective, i.e. inhibit fungus colonies.

Example B12
Action against *Colletotrichum lagenarium* on cucumbers

After a cultivation period of 2 weeks, cucumber plants are sprayed with a spray mixture (concentration: 0.002%) of the test compound. Two days later the plants are infected with a spore suspension ($1.5 \times 10^5$ spores/ml) of the fungus and incubated for 36 hours at 23° C. and high humidity. Incubation is then continued at normal humidity and c. 22°–23° C. Fungal infestation is evaluated 8 days after infection. Infestation of untreated and infected control plants is 100%.

Some of the compounds of formula I, in particular compounds 3.1 and 3.17, inhibit infestation almost completely.

Example B13
Action against *Fusarium novale* on rye

Rye of the Tetrahell variety which is naturally infected with *Fusarium nivale* is dressed on a mixer roll with the test fungicide using the following concentrations: 20 or 6 ppm a.i. (based on the weight of the seeds).

The infected and treated rye is sown in October in a field trial with a mechanical sower in plots of 3 m in length and in 6 furrows. Three replicates are carried out at each concentration.

The plants are cultivated under normal field conditions (preferably in a region with closed snow cover during the winter months) until evaluation is made.

The phytotoxicity is determined by assessing emergence in the autumn and population density/tillering in the spring.

Activity is assessed by making a percentage count of the plants infested by Fusarium in the spring immediately after the thaw. The number of infected plants was less than 5% in this trial. The emerged plants had a healthy appearance.

Example B14
Action against *Septoria nodorum* on wheat

Wheat plants in the 3-leaf stage are sprayed with a spray mixture prepared from a wettable powder formulation of the test compounds (2.8:1) at a rate of application of 60 ppm.

The treated plants are infected 24 hours later with a conidia suspension of the fungus. The plants are then incubated for 2 days at 90–100% relative humidity and stood in a greenhouse for another 10 days at 20°–24° C. Evaluation of fungus infestation is made 13 days later. Infestation is less than 1% on the wheat plants.

Example B15
Action against *Rhizoctonia solani* on rice plants
a) Protective-local soil application 10-day-old rice plants are drenched with a suspension prepared from a formulation of the test compound (spray mixture) without contaminating the growing parts of the plants. Infection is made 3 days later by placing in each pot a barley straw stalk infected with *Rhizoctonia solani* between the rice plants. The plants are incubated for 6 days at 29° C. (day) and 26° C. (night) and 95% relative humidity (humidity box) in a climatic chamber and then evaluation is made of the fungus infestation. Infestation of the rice plants was less than 5%. The plants had a healthy appearance.
b) Protective-local foliar application 12-day-old rice plants are sprayed with a suspension prepared from a formulation of the test compound. Infection is made 1 day later by placing in each pot a barley straw stalk infected with *Rhizoctonia solani* between the rice plants. The plants are incubated for 6 days at 29° C. (day) and 26°

C. (night) and 95% relative humidity (humidity box) in a climatic chamber and then evaluation is made of the fungus infestation. Infestation on untreated and infected plants is 100%. Some of the compounds of formula I inhibit infestation completely.

B. Insecticidal activity

Example B16
Action against *Aphis craccivora*

Pea seedlings are infested with Aphis craccivora and then sprayed with a spray mixture containing 100 ppm of test compound and incubated at 20° C. Evaluation is made 3 and 6 days later. The percentage reduction in the population (percentage kill) is determined by comparing the number of dead aphids on the treated plants with those on the untreated plants.

Compounds of Tables 3–7 are very effective in this test. In particular, compound 3.2 is more than 80% effective.

Example B17
Action against *Diabrotic balteata*

Maize seedlings are spayed with an aqueous emulsion spray formulation containing 100 ppm of test compound. After the spray coating has dried, the maize seedlings are populated with 10 larvae of *Diabrotica balteata* in the $L_2$ stage and put into a plastic container. Evaluation is made 6 days later. The percentage reduction in the population (percentage kill) is determined by comparing the number of surviving cicadas on the untreated plants with those on the untreated plants.

Compounds of Tables 3–7 are very effective in this test. In particular, compounds 3.1 and 3.3 are more than 80% effective.

Example B18
Action against *Heliothis virescens*

Young soybean plants are sprayed with an aqueous spray emulsion formulation containing 100 ppm of test compound. After the spray coating has dried, the soybean plants are populated with 10 caterpillars of *Heliothis virescens* in the first stage and put into a plastic container. Evaluation is made 6 days later. The percentage reduction in the population (percentage kill) is determined by comparing the number of dead caterpillars and the feeding damage on the treated plants with those on the untreated plants. Compounds of Tables 3–7 are very effective in this test. In particular, compound 3.3 is more than 80% effective.

Example B19
Action against *Spodoptera littoralis*

Young soybean plants are sprayed with an aqueous spray emulsion formulation containing 100 ppm of test compound. After the spray coating has dried, the soybean plant are populated with 10 caterpillars in the $L_3$ stage of *Heliothis virescens* and put into a plastic container. Evaluation is made 3 days later. The percentage reduction in the population (percentage kill) is determined by comparing the number of dead caterpillars and the feeding damage on the treated plants with those on the untreated plants.

Compounds of Tables 3–7 are very effective in this test. In particular, compounds 3.1, 3.2 and 3.3 are more than 80% effective.

C. Acaricidal action

Example B20
Action against *Tetranychus urticae*

Young bean plants are populated with a mixed population of *Tetranychus urticae* and sprayed 1 day later with an aqueous emulsion spray formulation containing 100 ppm of test compound. The plants are then incubated for 6 days at 25° C. and afterwards evaluated. The percentage reduction in the population (percentage kill) is determined by comparing the number of dead eggs, larvae and adults on the treated plants with those on the untreated plants.

Compounds of Tables 3–7 show good activity in this test. In particular, compounds 3.1, 3.2 and 3.3 are more than 80% effective.

What is claimed is:

1. A compound of formula

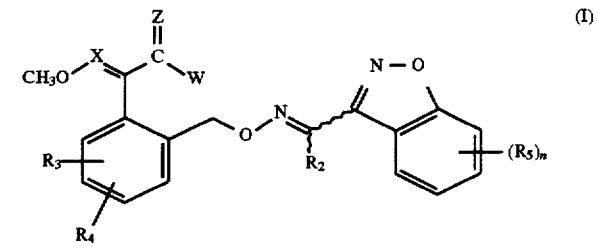

wherein
a) X is CH, Z is oxygen and W is $OR_1$; or
b) X is nitrogen, Z is oxygen and W is $OR_1$; or
c) X is nitrogen, Z is oxygen, sulfur or sulfoxide and W is the $NHR_1$ group; and the other substituents have the following meanings:

$R_1$ is $C_1$–$C_4$alkyl; $C_3$–$C_4$alkenyl; $C_3$–$C_4$alkynyl;

$R_2$ is H, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or CN;

$R_3$ and $R_4$ are each independently of the other H, $C_1$–$C_4$alkyl, $C_1$–$C_4$alkoxy, OH, CN, $NO_2$, $Si(CH_3)_3$, $CF_3$ or halogen;

n is 0, 1, 2, 3 or 4;

$R_5$ is halogen, $C_1$–$C_4$alkyl, halo-$C_1$–$C_4$alkyl, unsubstituted or mono- to tetrasubstituted $C_1$–$C_4$alkylenedioxy, the substituents being selected from the group consisting of $C_1$–$C_4$alkyl and halogen; CN, $NO_2$, $XR_6$, phenyl or chlorophenyl;

X is O, $O(C_1$–$C_4$alkylene), $(C_1$–$C_4$alkylene)O, $S(O)_m$, $S(O)_m(C_1$–$C_4$alkylene), $(C_1$–$C_4$alkylene)$S(O)_m$ or $C_1$–$C_4$alkylene;

m is 0, 1 or 2;

$R_6$ is $C_1$–$C_6$alkyl; halo-$C_1$–$C_6$alkyl; $C_3$–$C_6$cycloalkyl; CN; $C_1$–$C_4$alkylene-Si$(C_1$–$C_4$alkyl$)_3$; $C_2$–$C_6$alkenyl or $C_3$–$C_6$alkynyl which are each unsubstituted or substituted by 1 to 3 halogen atoms, or mono- to pentasubstituted aryl or heterocyclyl, the substituents being selected from the group consisting of halogen, $C_1$–$C_6$alkyl, halo-$C_1$–$C_6$alkyl, $C_1$–$C_6$alkoxy, halo-$C_1$–$C_6$alkoxy and CN; or

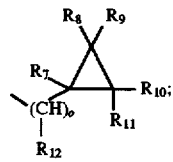

and wherein
$R_7$, $R_8$, $R_9$, $R_{10}$ and $R_{11}$ are each independently of one another H, halogen or $C_1$–$C_4$alkyl;

$R_{12}$ is H or $C_1$–$C_4$alkyl; and o is 0, 1, 2 or 3.

and, whenever obtained, an E/Z isomer thereof.

2. A compound of formula Ia according to claim 1

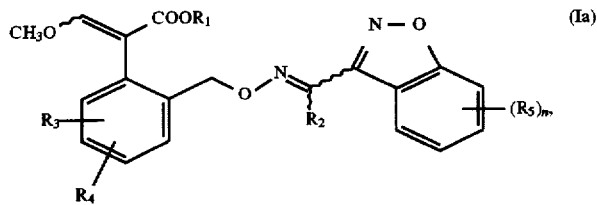

wherein $R_1$ is $C_1$–$C_4$alkyl;

$R_2$ is H, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or CN;

$R_3$ and $R_4$ are each independently of the other H, $C_1$–$C_4$alkyl, $C_1$–$C_4$alkoxy, OH, CN, $NO_2$, $Si(CH_3)_3$, $CF_3$ or halogen;

n is 0, 1, 2, 3 or 4;

$R_5$ is halogen, $C_1$–$C_4$alkyl, halo-$C_1$–$C_4$alkyl, unsubstituted or mono- to tetrasubstituted $C_1$–$C_4$alkylenedioxy, the substituents being selected from the group consisting of $C_1$–$C_4$alkyl and halogen; CN; $NO_2$ or $XR_6$;

X is O, O($C_1$–$C_4$alkylene), ($C_1$–$C_4$alkylene)O, $S(O)_m$, $S(O)_m$($C_1$–$C_4$alkylene), ($C_1$–$C_4$alkylene)$S(O)_m$ or $C_1$–$C_4$alkylene;

m is 0, 1 or 2;

$R_6$ is $C_1$–$C_6$alkyl, halo-$C_1$–$C_6$alkyl, $C_3$–$C_6$cycloalkyl, $C_2$–$C_6$alkenyl or $C_3$–$C_6$alkynyl which are each unsubstituted or substituted by 1 to 3 halogen atoms, unsubstituted or mono- to pentasubstituted aryl or heterocyclyl, the substituents being selected from the group consisting of halogen, $C_1$–$C_6$alkyl, halo-$C_1$–$C_6$alkyl, $C_1$–$C_6$alkoxy, halo-$C_1$–$C_6$alkoxy and CN; or

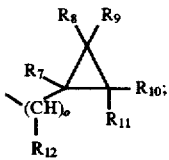

and wherein $R_7$, $R_8$, $R_9$, $R_{10}$ and $R_{11}$ are each independently of one another H, halogen or $C_1$–$C_4$alkyl;

$R_{12}$ is H or $C_1$–$C_4$alkyl; and o is 0, 1, 2 or 3.

3. A compound of formula Ib according to claim 1

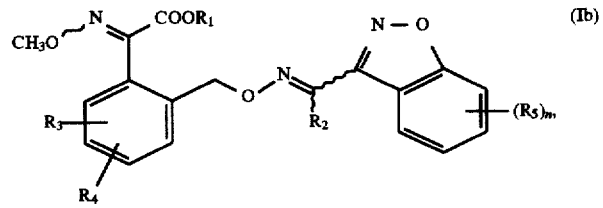

wherein $R_1$ is $C_1$–$C_4$alkyl;

$R_2$ is H, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or CN;

$R_3$ and $R_4$ are each independently of the other H, $C_1$–$C_4$alkyl, $C_1$–$C_4$alkoxy, OH, CN, $NO_2$, $Si(CH_3)_3$, $CF_3$ or halogen;

n is 0, 1, 2, 3 or 4;

$R_5$ is halogen, $C_1$–$C_4$alkyl, halo-$C_1$–$C_4$alkyl, unsubstituted or mono- to tetrasubstituted $C_1$–$C_4$alkylenedioxy, the substituents being selected from the group consisting of $C_1$–$C_4$alkyl and halogen; CN; $NO_2$ or $XR_6$, phenyl or chlorophenyl;

X is O, O($C_1$–$C_4$alkylene), ($C_1$–$C_4$alkylene)O, $S(O)_m$, $S(O)_m$($C_1$–$C_4$alkylene), ($C_1$–$C_4$alkylene)$S(O)_m$ or $C_1$–$C_4$alkylene;

m is 0, 1 or 2;

$R_6$ is $C_1$–$C_6$alkyl; halo-$C_1$–$C_6$alkyl; $C_3$–$C_6$cycloalkyl; CN; $C_1$–$C_4$alkylene-Si($C_1$–$C_4$alkyl)$_3$; $C_2$–$C_6$alkenyl or $C_3$–$C_6$alkynyl which are each unsubstituted or substituted by 1 to 3 halogen atoms, or mono- to pentasubstituted aryl or heterocyclyl, the substituents being selected from the group consisting of halogen, $C_1$–$C_6$alkyl, halo-$C_1$–$C_6$alkyl, $C_1$–$C_6$alkoxy, halo-$C_1$–$C_6$alkoxy and CN; or

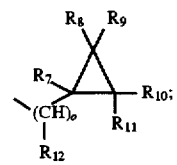

and wherein $R_7$, $R_8$, $R_9$, $R_{10}$ and $R_{11}$ are each independently of one another H, halogen or $C_1$–$C_4$alkyl;

$R_{12}$ is H or $C_1$–$C_4$alkyl; and o is 0, 1, 2 or 3.

4. A compound of formula Ic according to claim 1

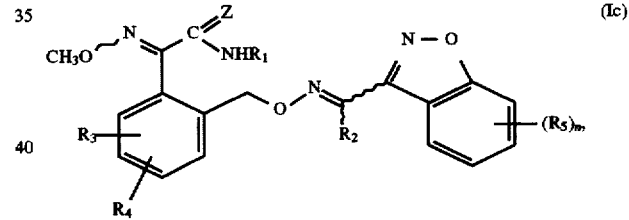

wherein $R_1$ is $C_1$–$C_4$alkyl; Z is oxygen, sulfur or sulfoxide;

$R_2$ is H, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or CN;

$R_3$ and $R_4$ are each independently of the other H, $C_1$–$C_4$alkyl, $C_1$–$C_4$alkoxy, OH, CN, $NO_2$, $Si(CH_3)_3$, $CF_3$ or halogen;

n is 0, 1, 2, 3 or 4;

$R_5$ is halogen, $C_1$–$C_4$alkyl, halo-$C_1$–$C_4$alkyl, unsubstituted or mono- to tetrasubstituted $C_1$–$C_4$alkylenedioxy, the substituents being selected from the group consisting of $C_1$–$C_4$alkyl and halogen; CN; $NO_2$ or $XR_6$;

X is O, O($C_1$–$C_4$-alkylene), ($C_1$–$C_4$alkylene)O, $S(O)_m$, $S(O)_m$($C_1$–$C_4$alkylene), ($C_1$–$C_4$alkylene)$S(O)_m$ or $C_1$–$C_4$alkylene;

m is 0, 1 or 2;

$R_6$ is $C_1$–$C_6$alkyl; halo-$C_1$–$C_6$alkyl; $C_3$–$C_6$cycloalkyl; CN; $C_1$–$C_4$alkylene-Si($C_1$–$C_4$alkyl)$_3$; $C_2$–$C_6$alkenyl or $C_3$–$C_6$alkynyl which are each unsubstituted or substituted by 1 to 3 halogen atoms, or mono- to pentasubstituted aryl or heterocyclyl, the substituents being selected from the group consisting of halogen, $C_1-C_6$alkyl, halo-$C_1-C_6$alkyl, $C_1-C_6$alkoxy, halo-$C_1-C_6$alkoxy and CN; or

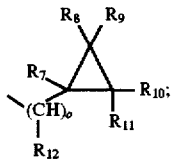

and wherein $R_7$, $R_8$, $R_9$, $R_{10}$ and $R_{11}$ are each independently of one another H, halogen or $C_1-C_4$alkyl;

$R_{12}$ is H or $C_1-C_4$alkyl; and o is 0, 1, 2 or 3.

5. A compound according to either claim 1 or claim 2 of formula I or Ia, wherein $R_1$ is $C_1-C_2$alkyl, or a possible E/Z isomer thereof.

6. A compound according to either claim 1 or claim 2 of formula I or Ia, wherein $R_3$ and $R_4$ are each independently of the other H, $C_1-C_2$alkyl, $C_1-C_2$alkoxy, $CF_3$ or halogen, or a possible E/Z isomer thereof.

7. A compound according to either claim 1 or claim 2 of formula I or Ia, wherein n is 0 or 1, or a possible E/Z isomer thereof.

8. A compound according to either claim 1 or claim 2 of formula I or Ia, wherein $R_5$ is halogen, $C_1-C_4$alkyl, halo-$C_1-C_4$alkyl, or $XR_6$, or a possible E/Z isomer thereof.

9. A compound according to either claim 1 or claim 2 of formula I or Ia, wherein X is O, O($C_1-C_2$alkylene), ($C_1-C_2$alkylene)O, $C_1-C_2$alkylene, or a possible E/Z isomer thereof.

10. A compound according to either claim 1 or claim 2 of formula I or Ia, wherein $R_1$ is $C_1-C_2$alkyl, $R_2$ is $C_1-C_2$alkyl, halo-$C_1-C_2$alkyl, cyclopropyl, $C_1-C_2$alkylthio or CN, $R_3$ and $R_4$ are each independently of the other H, $C_1-C_2$alkyl, $C_1-C_2$alkoxy, $CF_3$ or halogen, n is 0, 1 or 2, $R_5$ is halogen, $C_1-C_4$alkyl, halo-$C_1-C_4$alkyl or $XR_6$, X is O, O($C_1-C_2$alkylene) or ($C_1-C_2$alkylene)O, and $R_6$ is $C_1-C_2$alkyl, halo-$C_1-C_2$alkyl, cyclopropyl, $C_3-C_4$alkenyl or $C_3-C_4$alkynyl which are each unsubstituted or substituted by 1 to 3 halogen atoms, or unsubstituted or mono- or disubstituted phenyl, the substituents being selected from the group consisting of $C_1-C_2$alkyl, halo-$C_1-C_2$alkyl, $C_1-C_2$alkoxy, halo-$C_1-C_2$alkoxy, and CN, or

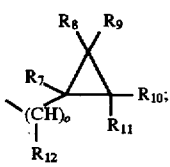

$R_7$ is H or methyl, $R_8$ and $R_9$ are each independently of the other bromo, chloro or fluoro, $R_{10}$, $R_{11}$ and $R_{12}$ are each independently of one another H oder $C_1-C_2$alkyl, and o is 0 or 1, or a possible E/Z isomer thereof.

11. A compound according to either claim 1 or claim 2 of formula I or Ia, wherein $R_1$ is methyl, $R_2$ is $C_1-C_2$alkyl, halomethyl, cyclopropyl, methylthio or CN, $R_3$ and $R_4$ are each independently of the other H, methyl, methoxy, chloro or fluoro, n is 0 or 1, $R_5$ is fluoro, chloro, $C_1-C_2$alkyl, halo-$C_1-C_2$alkyl or $XR_6$, X is O or O(methylene), and $R_6$ is methyl, halomethyl, $C_2-C_3$alkenyl or propynyl which are each unsubstituted or substituted by 1 or 2 halogen atoms, or unsubstituted or monosubstituted phenyl, the substituents being selected from the group consisting of halogen, methyl, halomethyl, methoxy and CN, or an E/Z isomer thereof.

12. Methyl 2-[[[(1-{1,2-benzisoxazol-3-yl}ethylidene)amino]oxy]methyl]-α-(methoxy-methylene)phenylacetate, methyl 2-[[[(1-{6-methoxy-1,2-benzisoxazol-3-yl}ethylidene)amino]oxy]methyl]-α-(methoxymethylene)phenylacetate, methyl 2-[[[(1-{6-[(2,2-dichlorocyclopropyl)methoxy]-1,2-benzisoxazol-3-yl}ethylidene)amino]oxy]methyl]-α-(methoxymethylene)phenylacetate, methyl α-(methoxymethylene)-2-[[[(1-{6-[3-(trifluoromethyl)benzyloxy]-1,2-benzisoxazol-3-yl}ethylidene)amino]oxy]methyl]phenylacetate, methyl α-(methoxymethylene)-2-[[[(1-{6-[2-propenyloxy]-1,2-benzisoxazol-3-yl}ethylidene)amino]oxy]methyl]phenylacetate, methyl α-(methoxymethylene)-2-[[[(1-{6-[2-propynyloxy]-1,2-benzisoxazol-3-yl}ethylidene)amino]oxy]methyl]phenylacetate, methyl α-(methoxymethylene)-2-[[[(1-{6-[4-(trifluoromethyl)benzyloxy]-1,2-benzisoxazol-3-yl}ethylidene)amino]oxy]methyl]phenylacetate, methyl α-(methoxymethylene)-2-[[[(1-{6-[2-(trifluoromethyl)benzyloxy]-1,2-benzisoxazol-3-yl}ethylidene)amino]oxy]methyl]phenylacetate, methyl 2-[[[(1-{5-methoxy-1,2-benzisoxazol-3-yl}ethylidene)amino]oxy]methyl]-α-(methoxymethylene)phenylacetate, 2-[[[(1-{6-[3,3-dichloro-2-propenyloxy]-1,2-benzisoxazol-3-yl}ethylidene)amino]oxy]-methyl]-α-(methoxymethylene)phenylacetate and the two E/Z isomers of methyl 2-[[[(1-{6-[1,1,2,3,3,3-hexafluoropropoxy]-1,2-benzisoxazol-3-yl}ethylidene)amino]oxy]meth-yl]-α-(methoxymethylene)phenylacetate.

13. A process for the preparation of a compound of formula I or of a possible E/Z isomer thereof, which comprises reacting a compound of formula

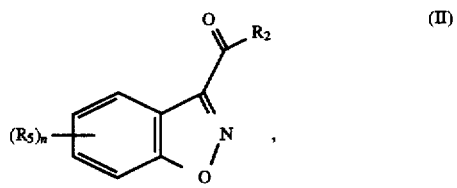

and wherein $R_2$ and $R_5$ are as defined for formula I optionally in the presence of a base, with hydroxylamine hydrochloride, and reacting the intermediate, which may or may not be isolated, in the presence of a base, with a compound of formula

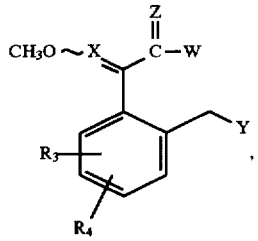

(III)

which is either known or can be prepared in analogy to corresponding known compounds, and wherein X, Z, W, $R_3$ and $R_4$ are as defined in connection with formula I, and Y is halogen, and, if desired, converting a compound of formula I obtainable by the process of the invention or in another manner or an E/Z isomer thereof into another compound of formula I or an E/Z isomer thereof, separating a mixture of E/Z isomers obtainable by the process of the invention and isolating the desired isomer.

14. A pesticidal composition which has a pesticidally effective amount of at least one compound of formula I as claimed in claim 1 or of a possible E/Z isomer thereof, together with at least one adjuvant.

15. A composition according to claim 14, wherein the pests are phytopathogenic microorganisms.

16. A composition according to claim 14, wherein the pests are insects and/or arachnids.

17. A process for the preparation of a composition according to claim 14 which comprises intimately mixing and/or grinding the active ingredient with at least one adjuvant.

18. A process for controlling pests which comprises applying thereto a composition as claimed in claim 14.

19. A process according to claim 18 wherein the pests are phytopathogenic microorganisms.

20. A process according to claim 18 wherein the pests are insects and/or arachnids.

21. A method of controlling pests, which comprises applying to said pests or to the locus liable to be infested a pesticidally effective amount of a compound according to claim 1.

22. A method according to claim 21 wherein the compound applied is a compound according to claim 2.

23. A method according to claim 21 wherein the locus liable to be infested is the propagation material.

24. Plant propagation material treated by the method according to claim 23.

* * * * *